US006742721B2

(12) United States Patent  (10) Patent No.: US 6,742,721 B2
Piper  (45) Date of Patent: Jun. 1, 2004

(54) SHOCK WAVE AEROSOLIZATION METHOD AND APPARATUS

(75) Inventor: Samuel David Piper, Sacramento, CA (US)

(73) Assignee: Evit Laboratories, McClellan, CA (US)

( * ) Notice: Subject to any disclaimer, the term of this patent is extended or adjusted under 35 U.S.C. 154(b) by 154 days.

(21) Appl. No.: 09/963,886

(22) Filed: Sep. 25, 2001

(65) Prior Publication Data

US 2002/0056760 A1 May 16, 2002

Related U.S. Application Data

(60) Provisional application No. 60/305,088, filed on Jul. 12, 2001, and provisional application No. 60/235,597, filed on Sep. 25, 2000.

(51) Int. Cl.$^7$ .................. B63H 11/00; B63H 11/10; B63H 25/46
(52) U.S. Cl. ............... 239/265.11; 239/265.17; 239/265.19; 239/265.23; 239/265.27
(58) Field of Search .............. 239/265.11, 265.17, 239/265.19, 265.23, 265.27, 271, 272, 302, 309, 310, 311, 366, 368, 369; 604/522, 68, 70, 56, 60, 58, 72; 222/631, 389

(56) References Cited

U.S. PATENT DOCUMENTS

| 4,114,615 | A |   | 9/1978 | Wetterlin |
| 5,483,953 | A |   | 1/1996 | Cooper |
| 5,630,796 | A | * | 5/1997 | Bellhouse et al. .......... 604/518 |
| 5,899,880 | A | * | 5/1999 | Bellhouse et al. ............ 604/70 |
| 6,009,869 | A |   | 1/2000 | Corbell |
| 6,010,478 | A | * | 1/2000 | Bellhouse et al. ............ 604/70 |
| 6,168,587 | B1 | * | 1/2001 | Bellhouse et al. .......... 604/522 |

FOREIGN PATENT DOCUMENTS

WO    WO 97/48496    6/1997

* cited by examiner

Primary Examiner—Davis Hwu
(74) Attorney, Agent, or Firm—John P. O'Banion

(57) ABSTRACT

A pneumatic inhaler that is able to deliver a controlled burst or dose of aerosol from a reservoir of liquid medication. The inhaler is suitable for the aerosolization of liquid medication that is in solution or suspension form. The inhaler is also ideal for the delivery of unique and specialty liquid medications in short aerosol bursts because no additional formulation development is needed and has the further advantage of being able to deliver multiple medications, as mixed by the patient, doctor, or pharmacist, with a single burst at a repeatable output. Because medication and propellant are not mixed until aerosolization occurs, the inhaler is appropriate for more pharmaceutical agents than the current inhalers available and at a substantial cost savings.

88 Claims, 29 Drawing Sheets

SHOCK WAVE AEROSOLIZATION METHOD AND APPARATUS

CROSS-REFERENCE TO RELATED APPLICATIONS

This application claims priority from U.S. provisional application serial No. 60/235,597 filed on Sep. 25, 2000 and from U.S. provisional application serial No. 60/305,088 filed on Jul. 12, 2001.

STATEMENT REGARDING FEDERALLY SPONSORED RESEARCH OR DEVELOPMENT

Not Applicable

REFERENCE TO A COMPUTER PROGRAM APPENDIX

Not Applicable

BACKGROUND OF THE INVENTION

1. Field of the Invention

This invention pertains generally to aerosol generating devices, and more particularly to inhalers which may be used to dispense liquid medication in short bursts of aerosol.

2. Description of the Background Art

Some medicines cannot withstand the environment of the digestive tract and must be delivered to the bloodstream intravenously or by some other means. One effective means for delivery of such medications to the blood stream is through the membranes and air passageways of the lung.

Inhalers of various types have been widely used for inhalation delivery of aerosols containing medication or other constituents to the conductive airways of the lung and the gas exchange regions of the deep lung. Aerosols are relatively stable suspensions of finely divided droplets or solid particles in a gaseous medium. When inhaled, aerosol particles may be deposited by contact upon the various surfaces of the respiratory tract leading to the absorption of the particles through the membranes of the lung into the blood stream and providing the desirable therapeutic action, or planned diagnostic behavior depending on the particular properties of the particles.

Because of the high permeability of the membranes of the lung and the copious flow of blood through the lung, medications deposed in the lung can readily enter the blood stream for action throughout the body. This may also allow for lower initial doses than would be required to be taken orally to achieve the desired concentration of medication in the blood. Other medications can directly influence the airway epithelium and effect responses via various airway receptors.

Properly generated and formulated aerosols can therefore be helpful in medical treatment. Inhalable aerosol particles capable of deposition within the lung are those with an aerodynamic equivalent diameter between 1 and 5 micrometers.

Still other types of aerosol particles deposited in the lung can act as tracers of airflow or indicators of lung responses and otherwise be a valuable diagnostic tool.

An inhaler produces a burst of aerosol consisting of fine particles intended for inhalation by a patient with a single breath. Inhalers are popular aerosol delivery devices because they are generally portable and are convenient to use. The particle size of the aerosol emitted from a typical inhaler is required to be considerably smaller than a conventional spray atomizer to ensure the appropriate deposition within the lungs. Atomizers are typically equipped with reservoirs, nozzles, and bulbs. Upon squeezing the bulb, liquid medication, which is placed within the reservoir, is entrained and sprayed by the nozzle for inhalation by the patient. However, the particle size produced by atomizers is too large for effective deposition in the lungs, although variants of the technique are still used for deposition of topical medication into the nasal cavity and associated tissues. A further disadvantage of atomizers is that they are unable to deliver a consistent dose due to discrepancies in user technique and the duration of each burst. Accordingly, atomizers are appropriate for delivery of medication to the sinus cavity, where the larger aerosol particle size is more effective for deposition but inappropriate for deposition in the deep lung.

Inhalers known in the art employ several techniques to achieve effective aerosolization of medicines for deposition in the lung. Commonly, inhalers are pre-packaged containers containing a mixture of medication to be aerosolized and a low saturation pressure vapor or gas, such as chlorofluorocarbons (CFCs), which are used as a propellant. The canister carrying the mixture of medication and propellant is equipped with a valve. When the valve is actuated, the inhaler dispenses a set amount of liquid and medication through a jet orifice, creating a spray. Upon release into the atmosphere, the low saturation pressure propellant is able to evaporate quickly leaving small aerosol particles of medication that are suitable for immediate inhalation. One disadvantage to this approach is that the propellant and the medication must be mixed for a significant period of time prior to inhalation by the patient, making them unsuitable for many medications. Furthermore, the pre-mixing of the medication and the propellant requires a different approach to gain regulatory approval, necessitating significant development time and capital, thereby significantly increasing the ultimate cost to the patient than with liquid formulations of same medication. To prevent agglomeration of the medication within the canister, surfactants are also added to the formulation, which often leave an undesirable taste in the mouth of the patient after inhalation.

Another inhaler strategy increasingly being employed is the aerosolization of dry medicament powders. Medicinal powders are prepared in advance and placed in a reservoir within the inhaler, or within blister pouches. Blister pouches have the advantage of being able to better preserve the powder from contamination and moisture. When the patient is ready for a dose of medication, they either access the reservoir to dispense an appropriate amount of powdered medication, or puncture a blister pouch containing the powder medicament. Aerosolization is typically achieved by the gas flow produced by the inhalation of the patient. However, the aerosolization of medicinal powders is plagued by problems of moisture contamination and the inconsistencies in inhalation effort by the patient from dose to dose. Furthermore, powder formulations are as expensive to develop as pre-mixed propellants.

A third inhaler strategy employs ultrasonic energy to aerosolize bursts of liquid medication. These devices require precise electronic valves and associated electronic circuitry, making them expensive to manufacture and prone to malfunction. Additionally, the particle size of the aerosol produced by these devices is often too large for optimal deposition in the lung.

Therefore, a need exists for a technology which can deliver aerosol bursts of liquid medication at a particle size that is appropriate for lung deposition and which is inexpensive for the patient, produces consistent output, uses a formulation which is inexpensive to develop and produce, that is reliable, that is easy to use, and which does not require the mixing of medication and propellant until the moment of aerosolization. The present invention satisfies this need, as well as others and has the further advantages of providing superior aerosol quality, and being lightweight and portable.

BRIEF SUMMARY OF THE INVENTION

The present invention generally pertains to a pneumatic inhaler that is able to deliver a controlled burst or dose of aerosol from a reservoir of liquid medication. The invention is appropriate for the aerosolization of liquid medication that is in solution or in suspension form. The invention is also ideal for the delivery of unique and specialty liquid medications in short aerosol bursts because no additional formulation development is needed. The apparatus has the further advantage of being able to deliver multiple medications, as mixed by the patient, doctor, or pharmacist, with a single burst of aerosol at a repeatable output. Because the medication and the propellant are not mixed until aerosolization occurs, the current invention is appropriate for more pharmaceutical agents than can be used by currently available inhalers at a substantial cost savings.

By way of example and not of limitation, a first embodiment of the present invention employs a cartridge or cylinder for containing virtually any type of compressed gas. Typically, carbon dioxide gas is used at a preferred pressure of approximately 750 psi, because the gas has a low critical temperature and pressure, allowing a small canister to carry significantly more than if filled with many other gases. The compressed gas is released in small bursts by a valve actuated by the patient, which delivers the gas to the supersonic shock nozzle. The nozzle comprises a jet orifice from which the compressed gas discharges into a sonic shock chamber. Provided that substantial backpressure is supplied, a supersonic jet exits from the jet orifice of the nozzle, which may be over expanded, under expanded or perfectly expanded. If the jet is over or under expanded, the supersonic jet, which remains at approximately the diameter of the jet orifice and which travels down the axis of the shock chamber, establishes a series of reflected compression and expansion shock waves. A perfectly expanded jet will have a cylindrical shock wave that envelops the entire jet. Although this would be preferable for the production of aerosol, it is impractical as a result of changes in supply pressure and the desired dimensional scale of the preferred embodiment of the current invention. Therefore, the nozzle is designed to be over expanded, and this is considered optimum.

Upon formation of the jet and the resulting reflected shock waves in the shock chamber, a vacuum is generated which causes liquid from the reservoir to be entrained through the liquid feed channels into the shock chamber. The preferred design channels the incoming fluid circumferentially around the shock chamber. Upon entrainment of the liquid into the shock chamber, the initially entrained liquid comes in contact with the shear forces created by the shock waves, producing copious amounts of aerosol particles suitable for inhalation. Shock waves are uniquely able to produce tremendous quantities of aerosol with good particle size for inhalation because they have the property of having large pressure differences over very small distances, thus making them able to generate substantial shear forces. The result of liquid traveling across this shock boundary is to be violently and physically disturbed, thus disintegrating into a dense burst of aerosol with appropriate particle size for inhalation. This represents a significant advance over traditional atomizers, which lacked the ability to produce shock waves of any design or magnitude, resulting in lower output and larger particle size.

Once the liquid has been entrained into the shock chamber and jet, the integrity of the jet and resulting reflecting shock waves is destroyed, resulting in a reduction in the subsequent production of aerosol particles than is produced in the initial burst. The subsequent production also has a generally larger particle size than the initial burst. The overall result is an initial burst of aerosol ideally suited for an inhaler, generally lasting less than a second. The output and particle size of such an inhaler is substantially better than would be predicted from the steady state operation of an atomizer or nebulizer nozzle of similar design. It is not possible to employ the same technique in the design and manufacture of an atomizer or nebulizer, because these devices are intended to run for durations of time longer than the first initial moments and the unique phenomena of the current invention only occurs at the moment of introduction of fluids to the reflected shock waves. Since the majority of aerosolization takes place in the first moment of liquid entrainment, little compressed gas is required for a burst of aerosol, making it possible, and efficient, to store enough carbon dioxide in a small canister for 200 bursts or more.

Although not of optimum design under most conditions, a similar result is obtained by having a shock region instead of a shock chamber. In such a design, the jet exits directly into a generally unenclosed region allowing the formation of reflected shock waves within the exiting jet. Liquid is entrained through one or more feed tubes placed proximally to the jet at a sufficient distance to generate a vacuum. Again, once the entrained liquid comes into contact with the reflected shock waves, a tremendous amount of aerosol particles are produced, and the integrity of the sonic jet and the shock waves is destroyed. Based on experimentation, such an approach was not found to be optimum because it did not allow for the precise introduction of fluid to the shock waves, which affects the output and particle size of the resulting aerosol burst. It should be noted that such an open design does have distinct advantages for thick, viscous fluids, because of the potential of clogging involved with the closed design, above first mentioned.

The preferred embodiment of the current invention draws liquid from a reservoir of medication that is preferably sufficient to hold 200 doses, and has been shown to produce reproducible doses of liquid medication. In the event that extremely precise dosing is desired, or if a change in dosing is desired from burst to burst, the current invention may be modified to consist of a small reservoir, or multiple small reservoirs, that contain the exact amount of liquid desired for delivery, and which is less than the nozzle will entrain with a given burst. Thus, the output of the inhaler is exactly equal to the contents of the reservoir, and may be easily changed from dose to dose.

Another approach that has been shown to be quite successful, is the use of blister packs pre-filled with the exact amount of liquid intended for aerosolization rather than the use of a reservoir. Prior to the contents of a blister cell being delivered, a feed tube, which is in fluid communication with the supersonic shock nozzle, is caused to puncture and penetrate the blister cell. Upon actuation of the nozzle, the contents of the blister cell is completely entrained into the shock nozzle and aerosolized. Blister packs also have the added advantage of better preserving medication than multiple dose reservoirs due to the limited exposure of the medication to air prior to aerosolization.

A complete discussion of the requirements for over, under, and perfectly expanded supersonic jets may be found in a text on compressible fluid dynamics. In general, the minimum pressure required to achieve supersonic flow in a nozzle is dependant upon the ambient discharge pressure and the supply pressure such that the ratio of the two should preferably be at least 0.5283 for air or oxygen and 0.5457 for carbon dioxide. Since all known inhalers have always discharged into roughly atmospheric conditions (14.7 psi), the resulting minimum supply pressure can be determined as being approximately equal to 27.8 psi or 13.1 psig for air or oxygen and 26.9 psi or 12.2 psig for carbon dioxide. In theory, these minimum supply pressures are sufficient to produce a flow of gas through the throat of a nozzle with a velocity equal to the speed of sound. In practice, higher pressures are required due to pressure losses and the expansion of gas into the internal volume of the device between the supply canister containing the stored gas and the choke of the nozzle. Although lower pressures above the calculated minimums will produce a degree of aerosolization, superior results are achieved with even higher pressures or continual increases in output for higher pressures. The increase in output for higher pressures is due to the increasing speed of the supersonic jet and the resulting increase in strength of the resulting shock waves. In the current embodiment of the invention, the pressure vessel is preferably filled with carbon dioxide to a pressure of approximately 750 psig, and the valve mechanism is designed to deliver a set amount of carbon dioxide with each actuation thereby controlling the repeatability of each dose and insuring that aerosol exiting the inhaler is produced primarily during the first few moments of contact between entrained liquid and the supersonic jet.

Supersonic jets produce shock waves in part because the jets don't expand gradually to the diameter of the shock chamber. Due to the nature of the fluid dynamics involved, and conservation of momentum, supersonic jets expand by producing shock waves, thus producing an extreme change in pressure from one side of a shock wave to the other. Unlike other exiting flow patterns, supersonic jets, through the dynamics of the shock waves, maintain roughly the same diameter that the jets had as they exited from the nozzle from which the jets were produced. Similarly, vacuum and entrainment of liquid is not primarily due to the Bernoulli principle, but more to boundary layer friction between the exiting jet and the surrounding gas in the shock chamber.

Any nozzle (orifice) which supplies a compressed gas to the nozzle at pressures above the calculated minimums will have a supersonic jet exiting from it which is either over, under, or perfectly expanded, provided that there is nothing present to disturb the jet, such as a liquid. A nozzle may achieve a velocity greater than the speed of sound if it is supplied with sufficient supply pressure and has a gradually increasing cross-sectional area downstream of the throat or choke. The potential increase in velocity with increasing cross-sectional area is dependant on the total supply pressure. For the perfectly expanded supersonic jet, the cross-sectional area is increased to the maximum possible for the given supply pressure, resulting in a supersonic jet with a shock wave entirely enveloping the jet. Although this is ideal for the production of aerosol, it is impractical in practice because of variance in the supply pressure and the dimensional tolerances required.

An under expanded supersonic jet has a maximum cross-sectional area which is less than the perfectly expanded supersonic jet. The extreme example of an under expanded jet is a simple orifice with no increasing cross sectional area. The result of a under expanded supersonic jet is a series of expansion and compression reflected shock waves, with the first shock waves immediately after the exit of the jet being expansion waves.

An over expanded supersonic jet has a maximum cross sectional area which is greater than the maximum cross sectional area of the perfectly expanded supersonic jet. The result is also a series of reflected compression and expansion shock waves. In the preferred embodiment, an over expanded supersonic jet is instigated by placing a large radius on the exit edge of the nozzle. Upon the jet traveling through the jet and then subsequently along the radius, the initial response is for the jet to increase to a speed greater than the speed of sound followed by an over expansion of the jet, which will produce reflected shock waves. An over expanded supersonic jet has the slight advantage over an under expanded supersonic jet in that the first reflected shock waves emanating from the exit plane of the jet are compression waves and not expansion waves. In general, compression waves produce higher shear forces and thus would be expected to produce more aerosol and a smaller particle sizes.

Once the entrained liquid is aerosolized, the momentum of the jet carries the aerosol into a mouthpiece for immediate inhalation by the patient. Depending on the ability of the patient to coordinate actuation and inhalation, and the desired portion of the lung targeted for deposition, a spacer or valved holding chamber may be attached to the mouthpiece. Spacers and chambers allow for easier coordination of patient's inhalation with device actuation, baffle out larger aerosol particles which are inappropriate for deposition within the lung, and allow more time for the liquid aerosol particles to evaporate, producing superior sized aerosol particles (1–3 microns) for deposition in the alveolar portions of the lung.

In accordance with another embodiment of the invention, a valve design is provided which is easier and less expensive to manufacture than in the previous embodiments. This embodiment includes a built in valved chamber for storing aerosol during inhalation, in contrast to the previous embodiments that allow for a chamber to be attached when desired. However, the invention is not limited to the use of a valved chamber or specific valve design.

The valved chamber stores aerosol upon actuation for subsequent inhalation in this embodiment. As is well known in the industry, and recently reported during in-vitro investigations (Respiratory Care, June 2000, Volume 45, Number 6, "Consensus Conference on Aerosols and Delivery Devices", page 628), valved chambers often maintain a static electric charge due to rinsing with water that causes a significant loss of aerosol particles due to mutual static electric attraction. This embodiment employs an anti-static plastic that prevents this phenomenon from occurring.

In addition to the properties described in the previous embodiments, the aerosolization process can be further optimized through placement of a liquid feed choke between the fluid reservoir containing the medication, and the liquid feeds that lead into the shock chamber. By further choking the flow of liquid down, it is possible to better control the introduction of fluid into the supersonic jet produced in the shock chamber, thus allowing for better aerosolization and an increase in the duration of the aerosol burst, although it is still a momentary phenomena relative to normal jet nebulization technologies.

Additionally, the shock wave aerosolization process functions remarkably well with micronized powder in blister packs as well. Blister packs, containing one or more cells, are used to store a pre-determined amount of liquid or powder. Prior to aerosolization, a feed tube, which is in fluid communication with the shock wave aerosolization process nozzle, is inserted into the blister pack cell. Subsequent to the insertion of the feed tube, the carbon dioxide valve is actuated, creating a set burst of gas. As previously described, the carbon dioxide exits the throat of the jet, causing a vacuum, which entrains the micronized powder or liquid through the feed tube and into the shock chamber. As previously described with liquid medication, when medicinal powder is entrained it becomes efficiently aerosolized in the reflected shock waves and carried out to the mouthpiece or valve chamber, as intended.

An object of the invention is to provide an inhaler, which can deliver a repeatable dose of aerosol containing particles appropriately sized for deposition within the patient's lung.

Another object of the invention is to provide an inhaler, which can produce aerosol particles appropriate for deposition in the bronchial airways.

Another object of the invention is to provide an inhaler, which can produce aerosol particles appropriate for deposition in the alveolar portions of the lung.

Another object of the invention is to provide an inhaler, which can aerosolize an aqueous solution.

Another object of the invention is to provide an inhaler, which can aerosolize a suspension of medication in liquid.

Another object of the invention is to provide an inhaler, which can aerosolize liquid pharmaceutical formulations currently available only for nebulizers.

Another object of the invention is to provide an inhaler, which does not mix medication and propellant prior to aerosolization.

Another object of the invention is to provide an inhaler, which can deliver combinations of different medications with one burst.

Another object of the invention is to provide an inhaler with an acceptable aftertaste.

Another object of the invention is to provide an inhaler, which is portable, convenient and easy to use.

Another object of the invention is to provide an inhaler, which is inexpensive to produce.

Another object of the invention is to provide an inhaler that has a built in valved chamber for storage of aerosol.

Another object of the invention is to provide an invention that works in conjunction with blister packs that contain either liquid or powder.

Further objects and advantages of the invention will be brought out in the following portions of the specification, wherein, the detailed description is for the purpose of fully disclosing preferred embodiments of the invention without placing limitations thereon.

BRIEF DESCRIPTION OF THE DRAWINGS

The invention will be more fully understood by reference to the following drawings that are for illustrative purposes only.

DETAILED DESCRIPTION OF THE INVENTION

Figure 1:
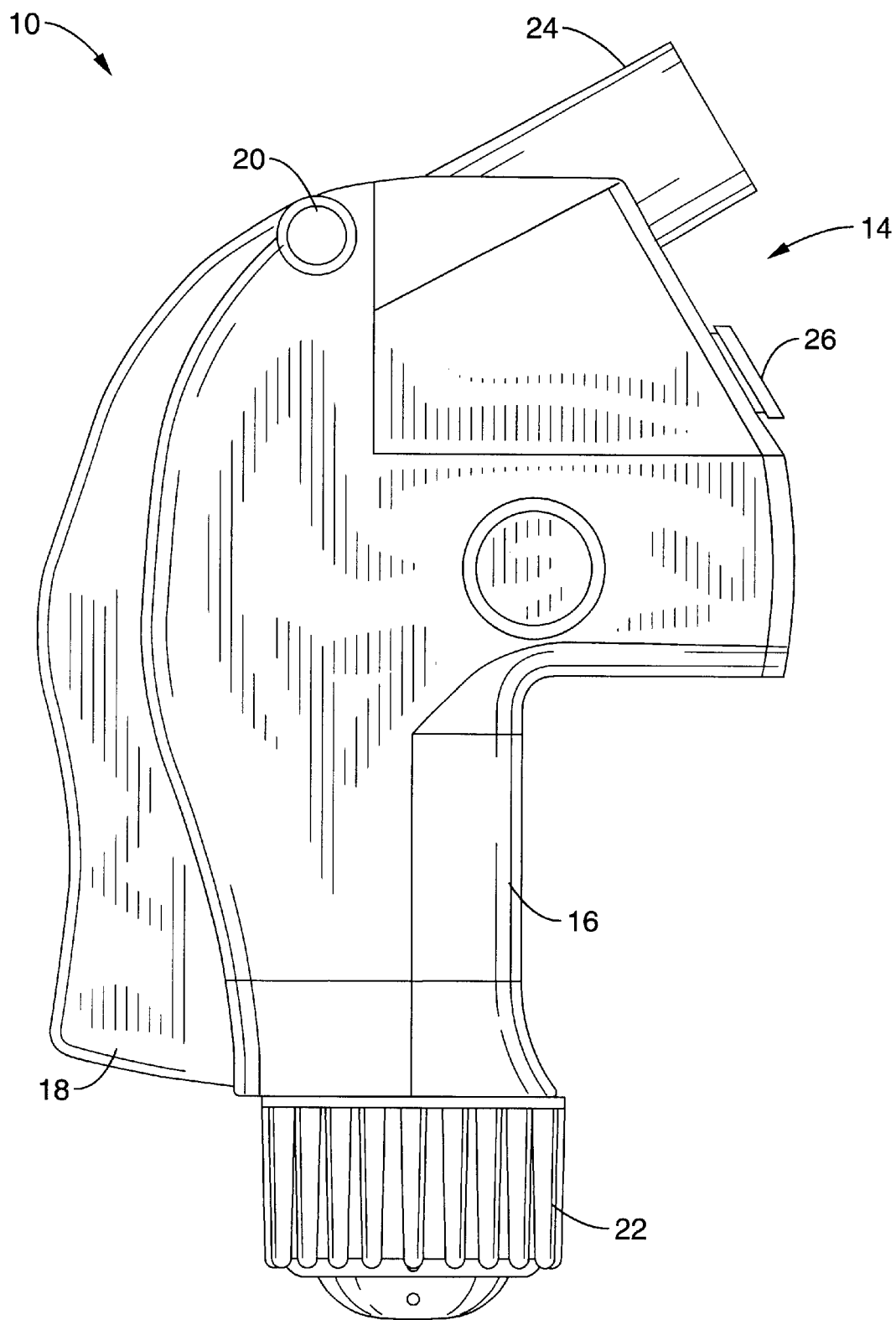
FIG. 1 is a side view of an embodiment of an inhaler according to the present invention.
Figure 2:
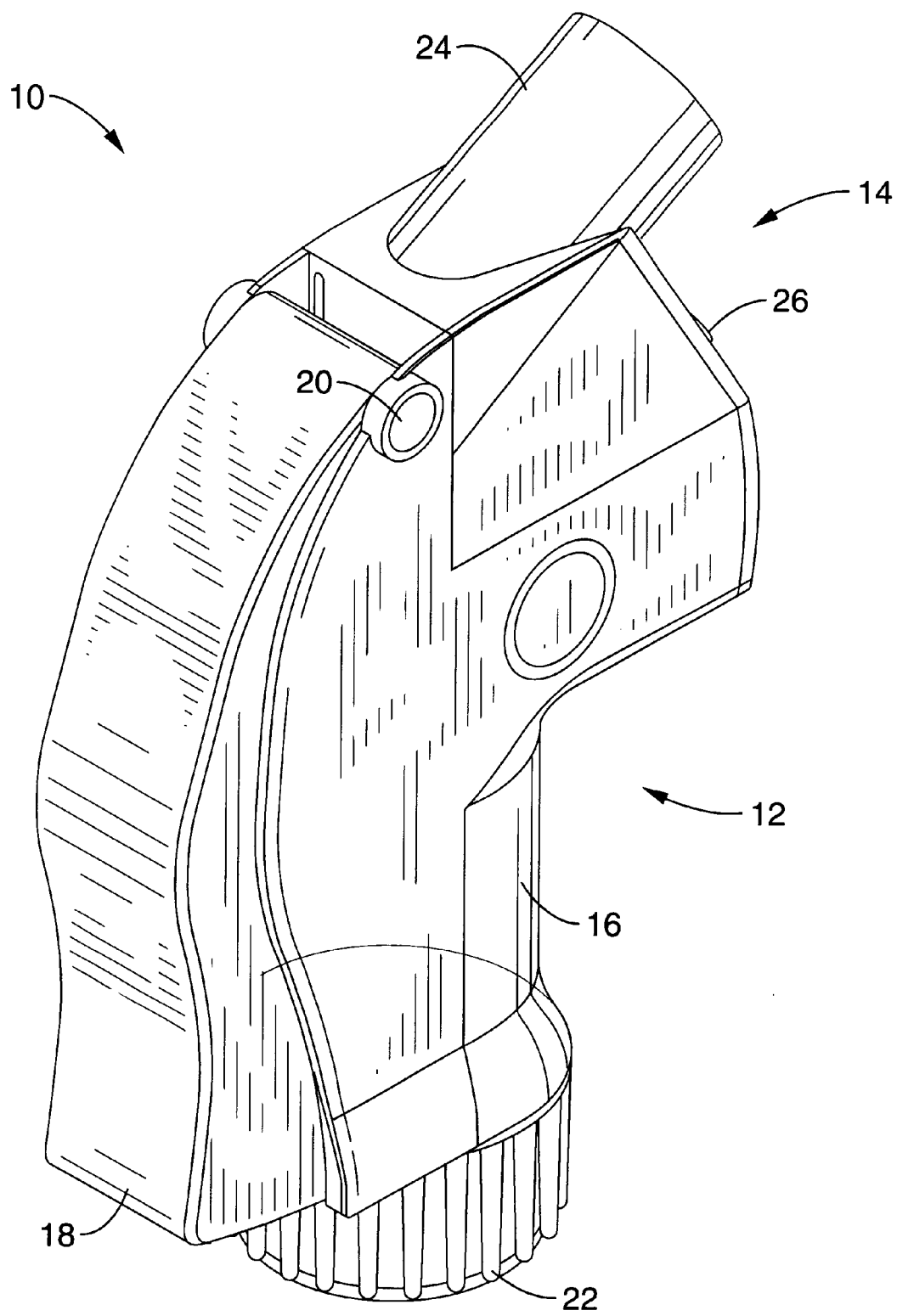
FIG. 2 is a perspective view of the inhaler of FIG. 1.
Figure 3:
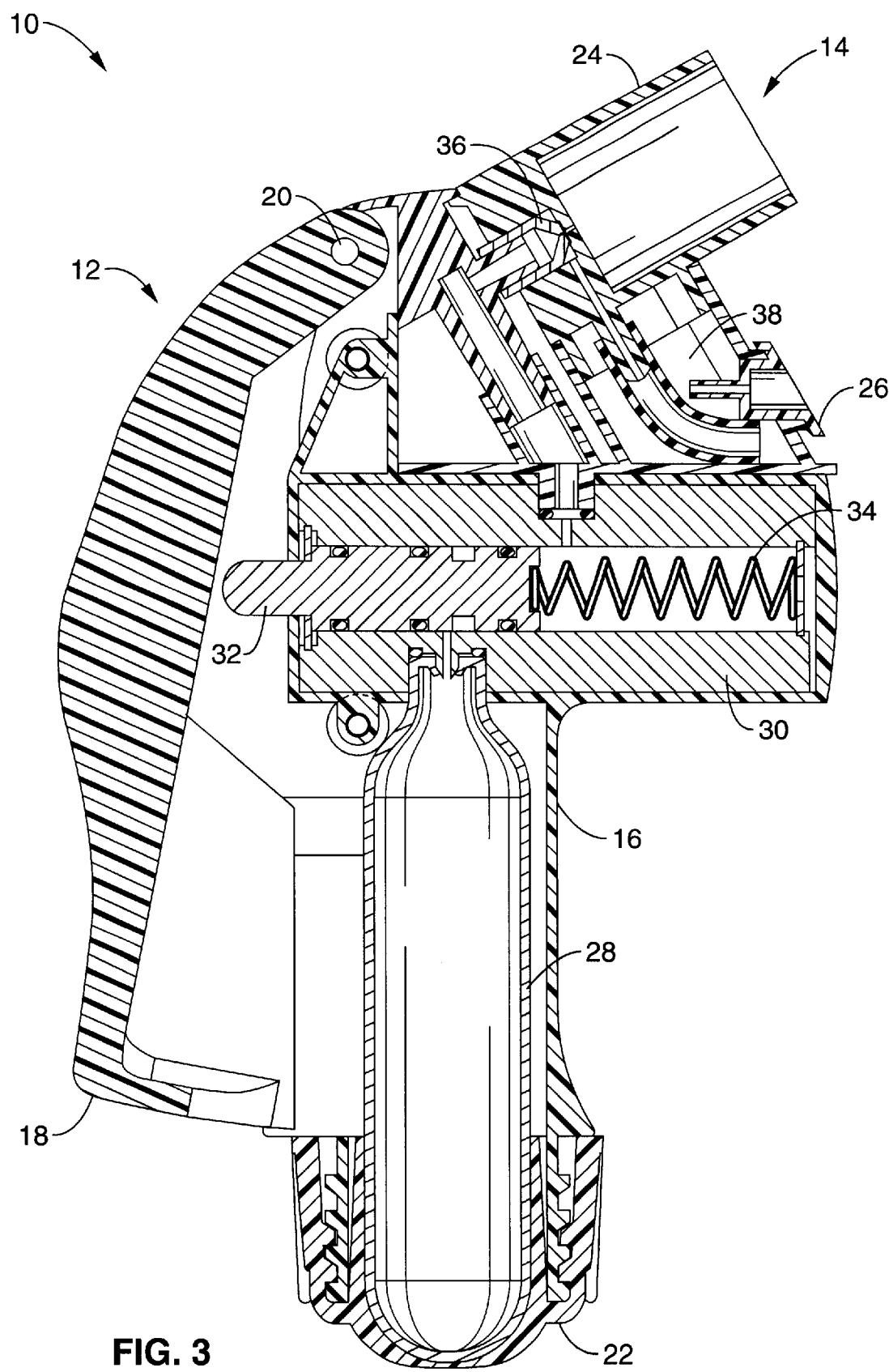
FIG. 3 is a side view in cross-section of the inhaler of FIG. 1.
Figure 10:
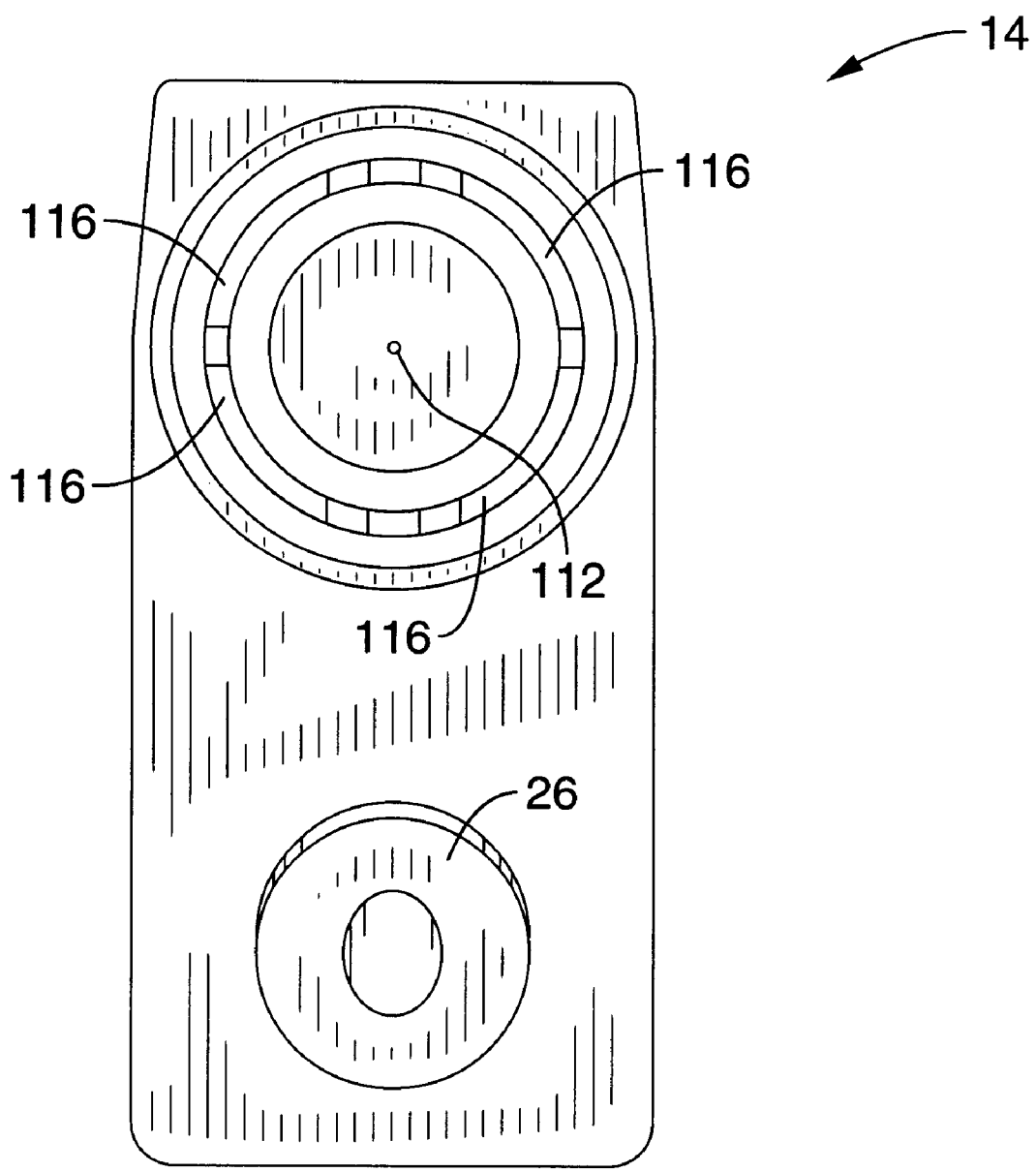
FIG. 10 is a front view of aerosol generator of FIG. 7.
Figure 11:
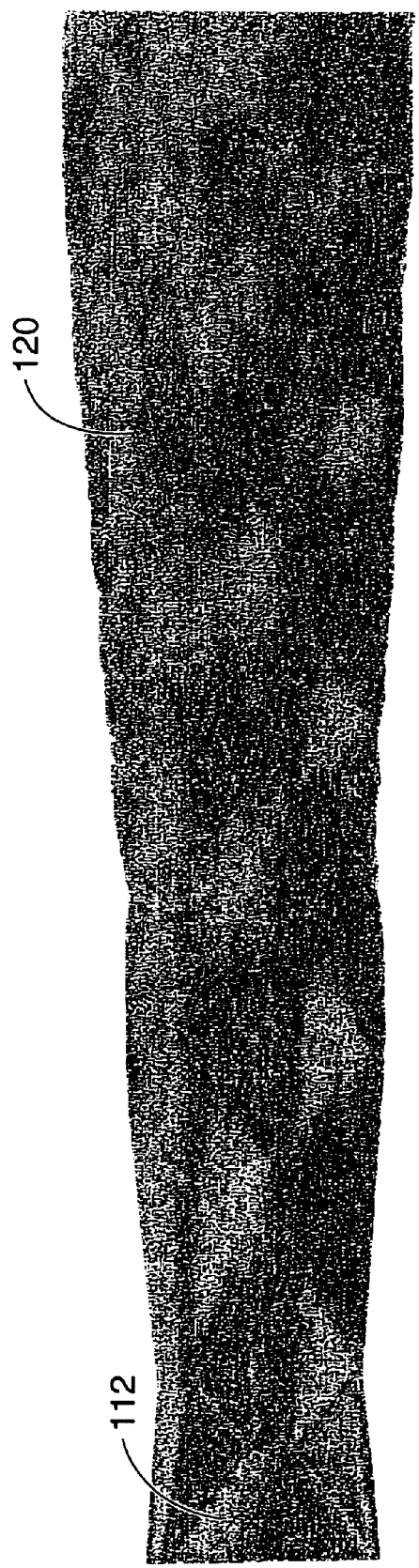
FIG. 11 is a rendering of an over expanded supersonic jet used in the inhaler of FIG. 1.
Figure 12:
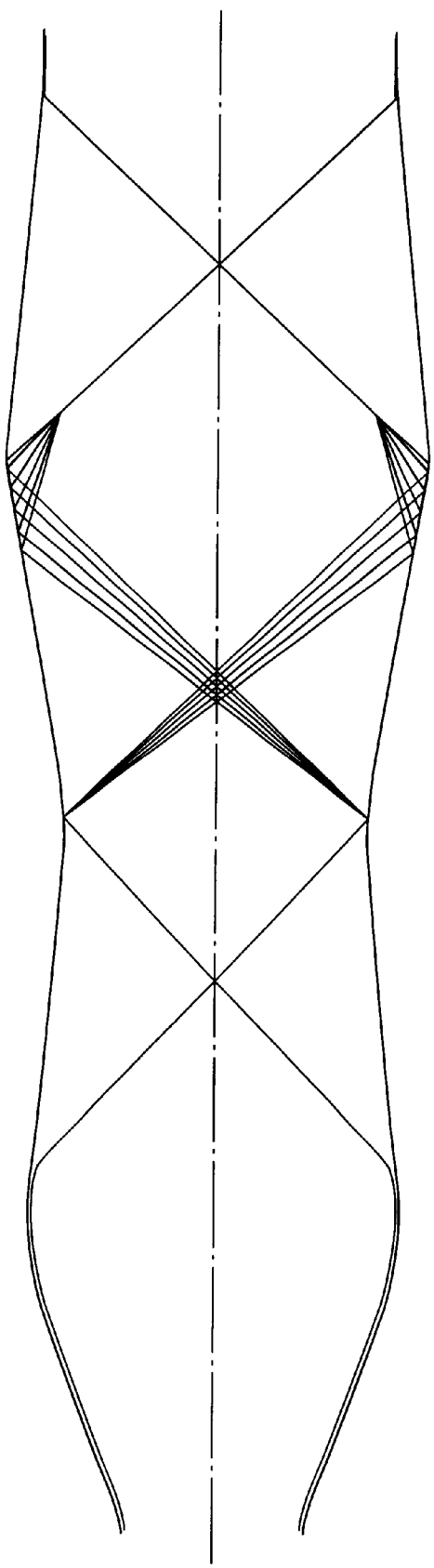
FIG. 12 is a schematic representation of the over expanded supersonic jet of FIG. 11.
Figure 13:
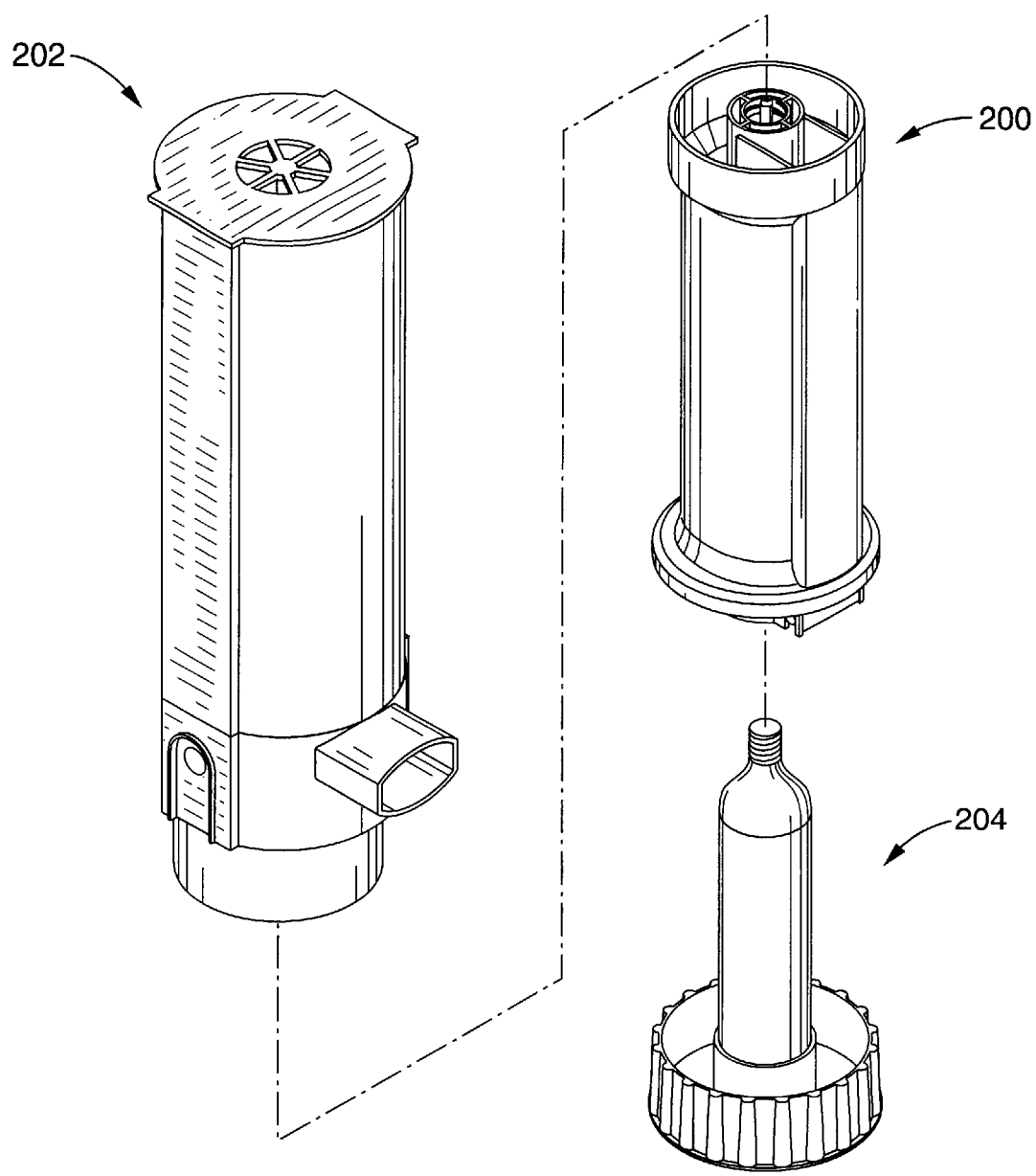
FIG. 13 is an exploded view of a second embodiment of an inhaler according to the present invention showing the reusable actuator handle, aerosol generator, and carbon dioxide cartridge.
Figure 14:
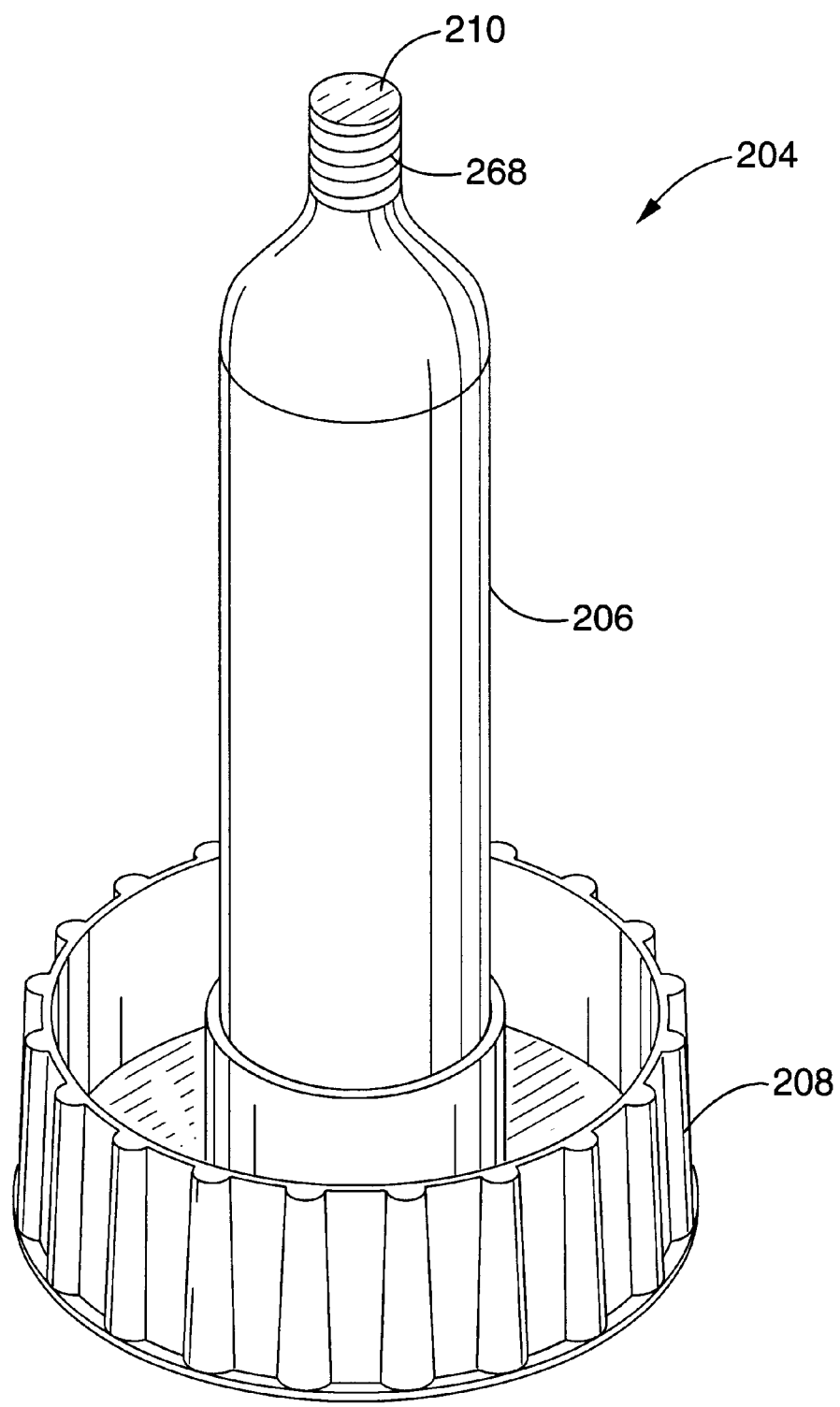
FIG. 14 is a perspective view of the disposable carbon dioxide refill cartridge portion of the inhaler of FIG. 13.
Figure 15:
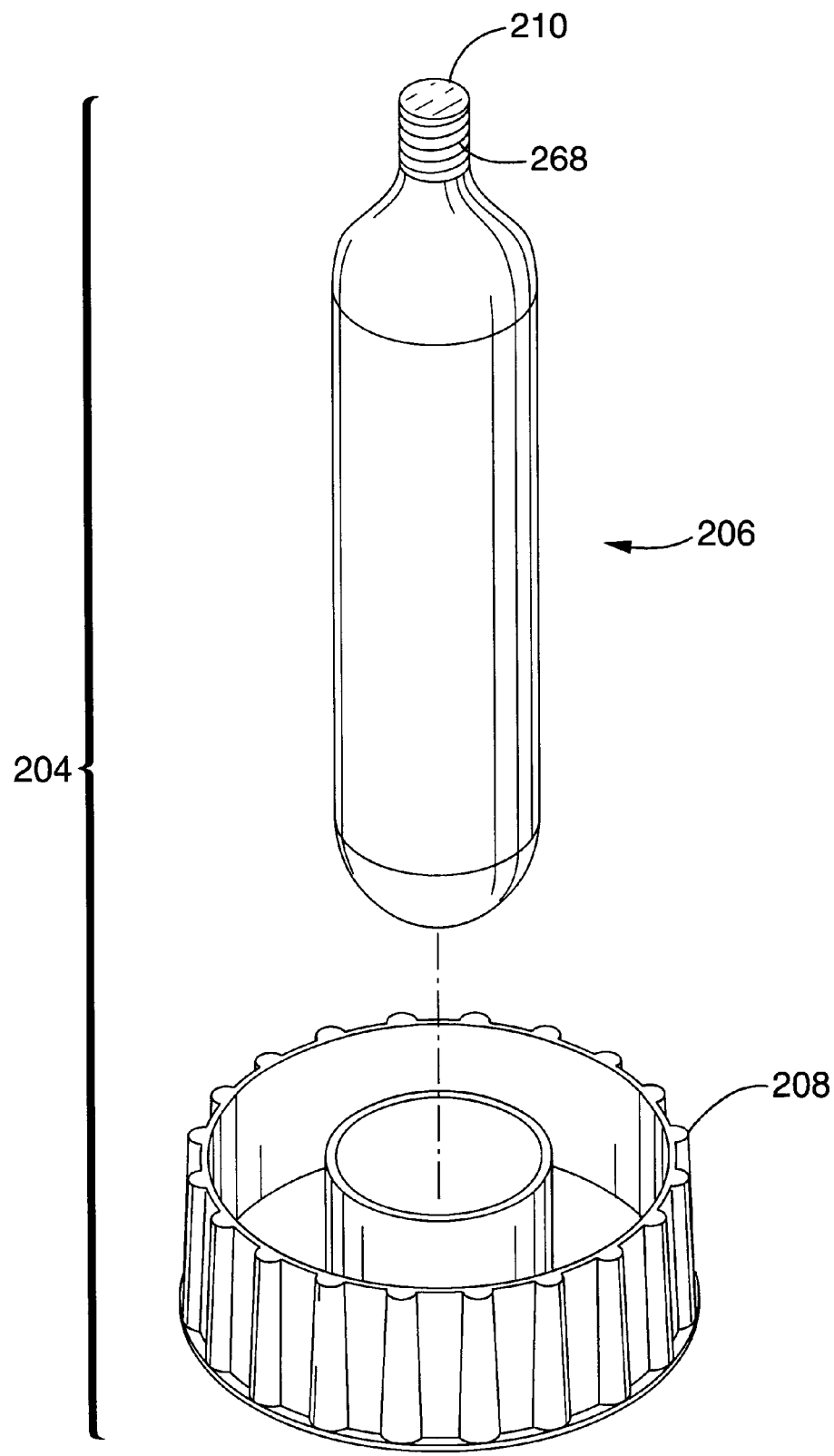
FIG. 15 is a exploded view of the carbon dioxide canister of FIG. 14.
Figure 16:
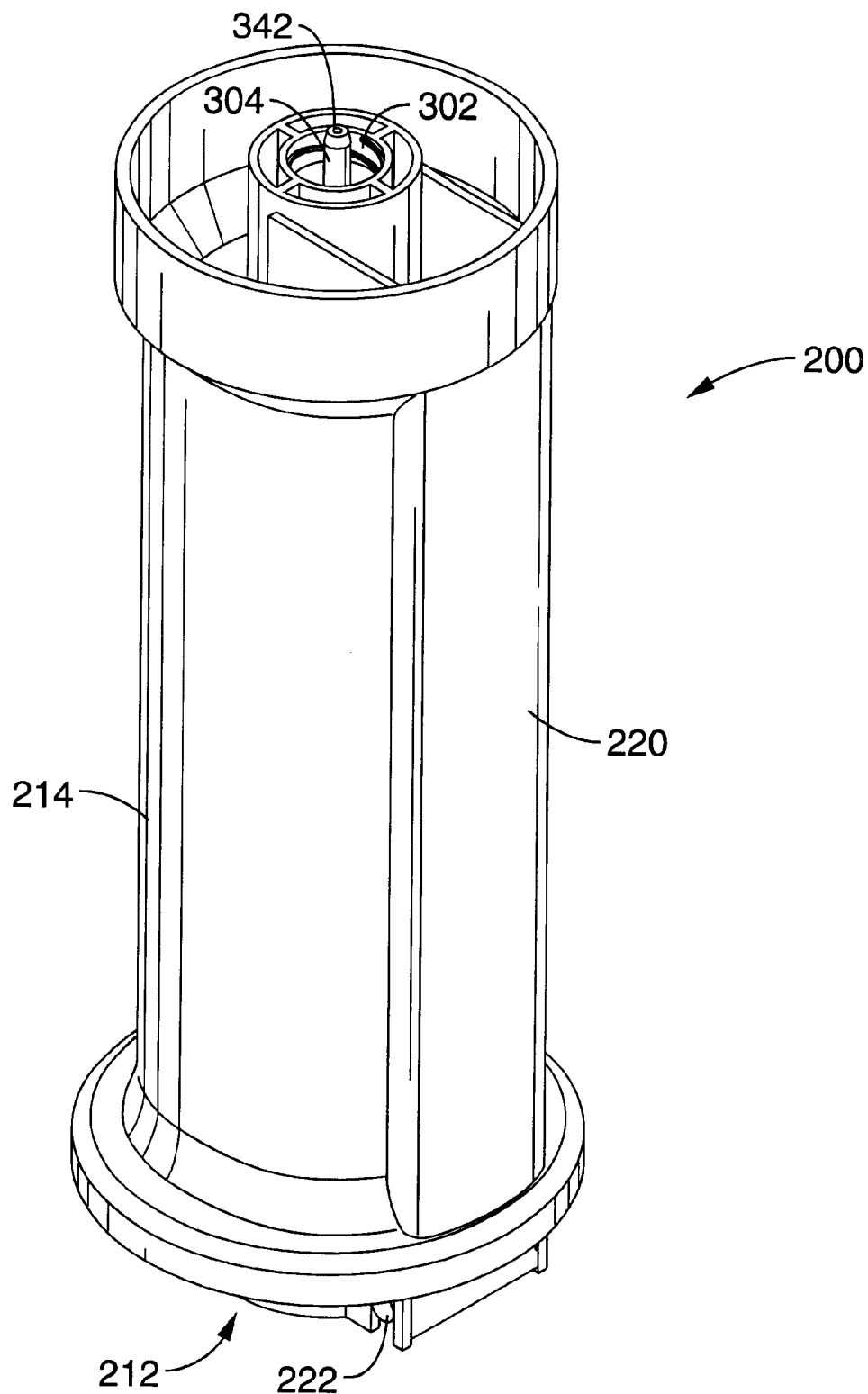
FIG. 16 is a perspective view of the reusable inhaler actuator portion of the inhaler of FIG. 13.
Figure 17:
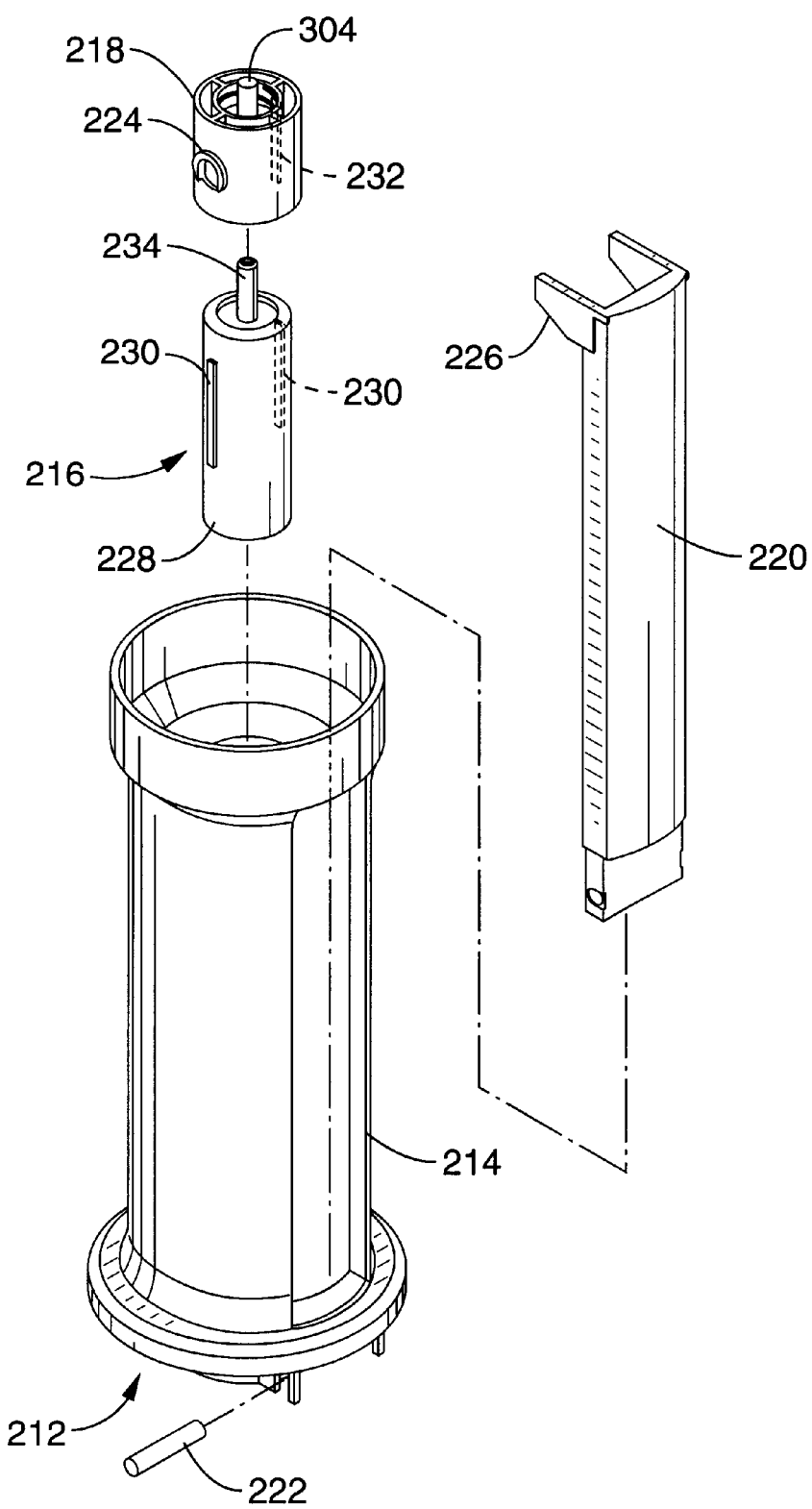
FIG. 17 is a exploded view of the reusable actuator of FIG. 16.
Figure 18:
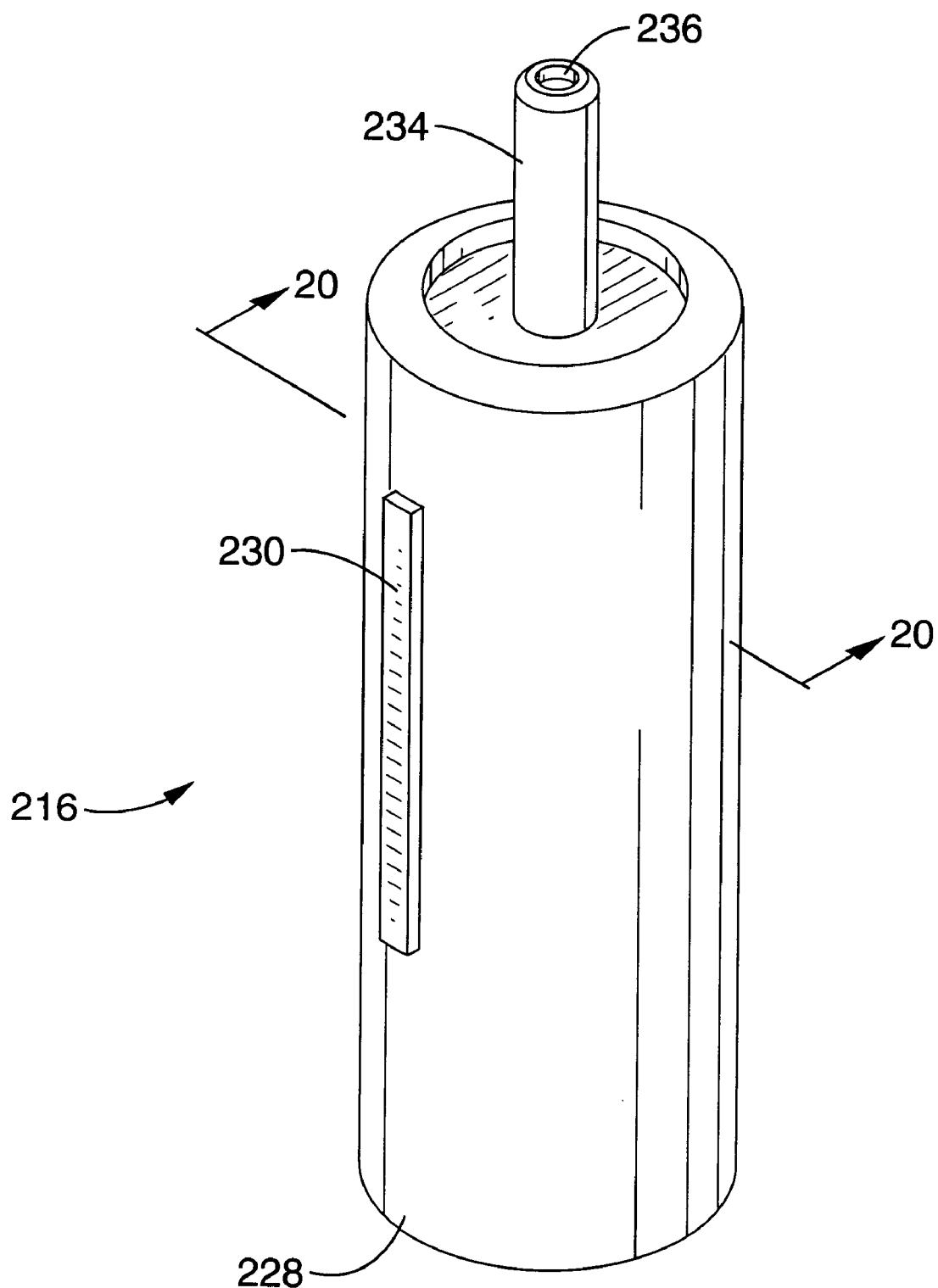
FIG. 18 is a perspective view of the valve portion of the inhaler of FIG. 13.
Figure 29:
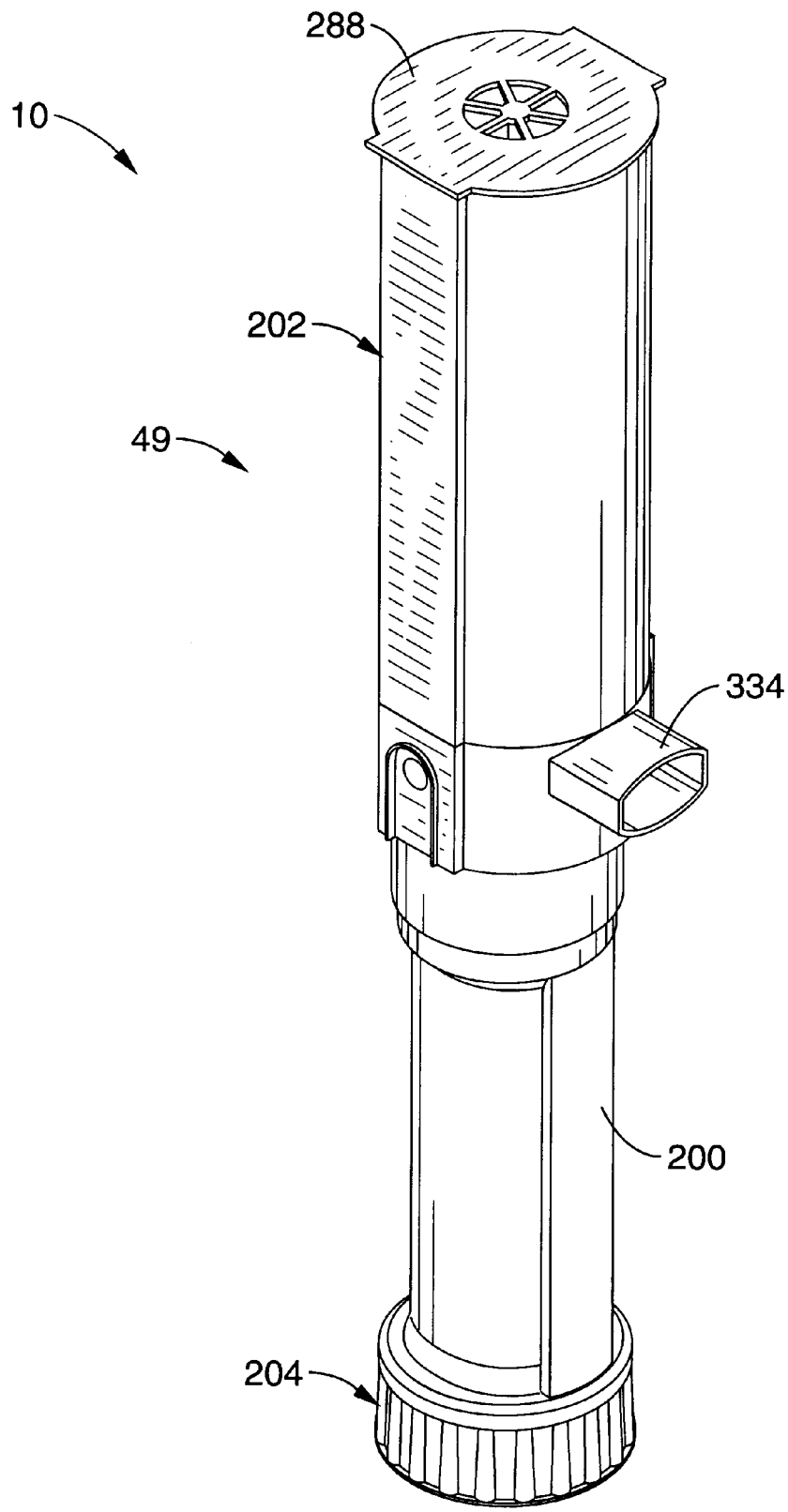
FIG. 29 is an assembled perspective view of the inhaler of FIG. 13.
Figure 30:
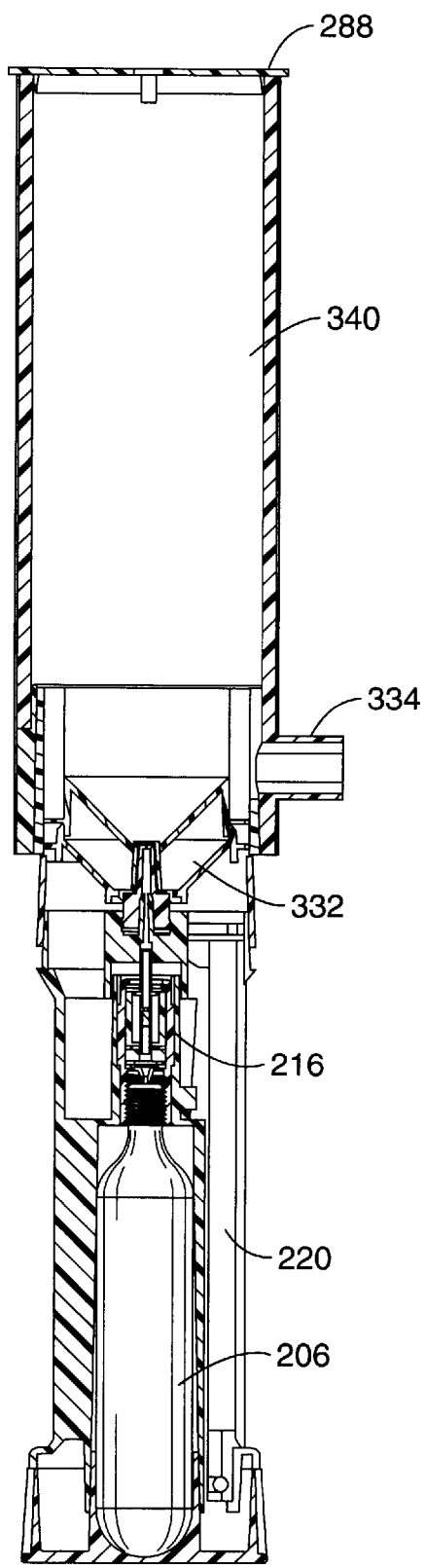
FIG. 30 is a side view in cross-section of the inhaler of FIG. 29.

FIG. 1 through FIG. 3 show the overall configuration of an embodiment of a shock wave aerosolization apparatus according to the present invention is shown. The inhaler portion of the apparatus comprises two primary parts; an actuator 12 shown in FIG. 4, FIG. 5, and more specifically in FIG. 6, and an aerosol generator 14 shown in FIG. 7, FIG. 8 and more specifically in FIG. 9 and FIG. 10. FIG. 11 and FIG. 12 are for illustrative purposes regarding the nature of reflected shock waves in a supersonic jet. FIG. 13 and FIG. 29 show the overall configuration of a second embodiment of the invention. FIG. 14 and FIG. 15 show the gas canister assembly. FIG. 16 through FIG. 20 detail the actuator handle assembly and FIG. 21 through FIGS. 28, 31 and 32 shows the aerosol generator assembly of the second embodiment. FIGS. 29 and 30 shows the configuration of the apparatus during use. FIG. 33 shows a third embodiment of the invention employing a supersonic shock nozzle assembly enclosed in a small disposable cartridge along with a single blister pack 352 containing sufficient medication for one aerosol treatment. It will be appreciated that the embodiments of the apparatus may vary as to configuration and as to details of the parts, and that the method may vary as to details of steps and their sequence, without departing from the basic concepts as disclosed herein.

Referring now to FIG. 1, the aerosolization apparatus 10 of the present invention generally includes an actuator 12 and an aerosol generator 14. The actuator 12 and the aerosol generator 14 are separable components in the embodiment shown, however, it will be understood that these components may be fully integrated and inseparable.

As seen in FIG. 2 and FIG. 3, the actuator 12 of apparatus 10 has a handle 16 that is preferably configured to fit in the notch between the thumb and first finger of the hand of the user. In the embodiment shown, the actuator 12 has a trigger 18 that pivots about trigger pin 20 and is brought toward the body of actuator 12 by the fingers of the user to actuate the device. The actuator 12 also has a cap 22 that can be removed from the body of the actuator 12 as needed.

The aerosol generator 14 is operably coupled with actuator 12 and provides aerosolized medications to a user through a mouthpiece 24 when the trigger 18 is depressed. Medicine is disposed within a reservoir through a port that is sealed with a plug 26.

Turning now to FIG. 3, a cross section of the apparatus 10 with the actuator 12 coupled with the aerosol generator 14 is shown. The primary components of the actuator 12 are the handle 16, cap 22, carbon dioxide canister 28, trigger 18, valve body 30, valve poppet 32, and valve spring 34. Carbon dioxide canister 28 is disposed within handle 16 and is held in place by cap 22.

The primary components of the aerosol generator 14 are reservoir 38, mouthpiece 24, aerosolization nozzle 36 and plug 26. It can be seen that canister 28 provides a source of supply of gas to the aerosol generator 14 that is regulated by poppet 32. Gas from the canister 28 is directed through the aerosolization nozzle 36, mixed with medicine from reservoir 38 and out through the mouthpiece 24 to the user.

Referring also to FIG. 4 and FIG. 5, the aerosol generator 14 is releasibly coupled with the actuator 12. The aerosol generator 14 component can be quickly removed from the actuator 12 for refilling and cleaning. Likewise, different medications can be administered sequentially to a single patient by removing the first aerosol generator 14 after the first dosage is administered and replacing it with a second aerosol generator 14 that has a different medication. Thus, it can be seen that a practitioner can administer appropriate medications to any number of patients using one actuator 12 and aerosol generators 14 specially prepared for each patient.

Turning now to FIG. 4, FIG. 5 and more specifically FIG. 6, actuator 12 is shown without the aerosol generator 12 in place. The actuator 12 is a source of gas supply that can be regulated by the actions of poppet 32. When cap 22 is removed from handle 16, carbon dioxide canister 28 can be placed into cap 22 and then inserted into the internal space of handle 16. With the tightening of cap 22, carbon dioxide canister 28 is caused to be punctured by hollow prong 40, which is part of valve body 30, and thereafter the canister is sealed against canister o-ring 42.

Once punctured and sealed, carbon dioxide canister 28 is in fluid communication with valve poppet 32 disposed within valve poppet chamber 46 through canister conduit 44 within hollow prong 40 and the wall of valve body 30.

Valve poppet 32 comprises a trigger head 48 with an actuating cam surface 50 that smoothly engages trigger 18 through the full range of motion of the trigger pull. The poppet 32 is biased to the far left or "rest" position, as shown, by spring 34, such that shoulder 54 is caused to rest against stop plate 56. Spring 34 preferably fits within spring indent 58 at the distal end of poppet 32.

The valve poppet in the activated position is shown in FIG. 6. It will be seen that valve poppet 32 is caused to move to the right, or "actuated" position, when trigger 18 is squeezed, resulting in force being applied to actuating cam surface 50 of trigger head 48 of poppet 32 in opposition to the force of valve spring 34.

The body 52 of poppet 32 preferably has a first o-ring groove 60, a second o-ring groove 62, and a third o-ring groove 64 that are mated with first o-ring 66, second o-ring 68, and third o-ring 70 respectively. The poppet body 52 also has a charging volume groove 72, preferably positioned between the second o-ring groove 62 and the third o-ring groove 64. First o-ring groove 60, second o-ring groove 62, third o-ring groove 64, and charging volume 72 all consist of geometry which is circumferential to valve poppet 32, which is generally cylindrical in shape. O-rings 66, 68 and 70 are all made preferably of urethane, which is compatible with high-pressure carbon dioxide.

Although o-rings are preferred, it will be understood that other alternative sealing means known in the art may also be used to eliminate leakage of gas from the canister conduit 44 into poppet chamber 46 and out of the apparatus.

Referring more particularly to FIG. 5, it can be seen that when valve poppet 32 is in the rest position, as shown, the internal gas pressure of carbon dioxide canister 28 is in fluid communication with charging volume 72 and the space between poppet 32 and the walls of poppet chamber 46, between o-rings 68 and 70 through canister conduit 44, resulting in charging volume 72 being filled with carbon dioxide to the same pressure that is in carbon dioxide canister 28. The contents of carbon dioxide canister 28, and charging volume 72, is prevented from escaping around the valve poppet 32 into the ambient environment primarily by second o-ring 68 and third o-ring 70 that seal the sections of the chamber 46 between the o-rings.

As valve poppet 32 is moved into the actuated position, as shown in FIG. 6, second o-ring 68 passes over canister conduit 44, preventing further fluid communication between carbon dioxide canister 28 and charging volume 72, and third o-ring 70 is caused to pass over valve exit conduit 74, thus releasing the pressurized gas in charging volume 72 through valve exit conduit 74 to valve exit port 76. Second o-ring groove 62 and third o-ring groove 64 are preferably spaced apart from charging volume 72 so that the second o-ring 68 terminates fluid communication between carbon dioxide canister 28 and charging volume 72 prior to the third o-ring 70 passing over valve exit conduit 74, thus preventing the contents of carbon dioxide canister 28 from ever being in fluid communication with valve exit conduit 74 and valve exit port 76, and creating a burst of pressurized gas to be released from charging volume 72.

Obviously, charging volume 72 may be designed for different volumes allowing for different amounts of carbon dioxide being released with each actuation. It will also be seen that first o-ring 66 prevents escape of contents of carbon dioxide canister 28 around valve poppet 32 into the ambient environment when valve poppet 32 is in the actuated position.

Figure 4:
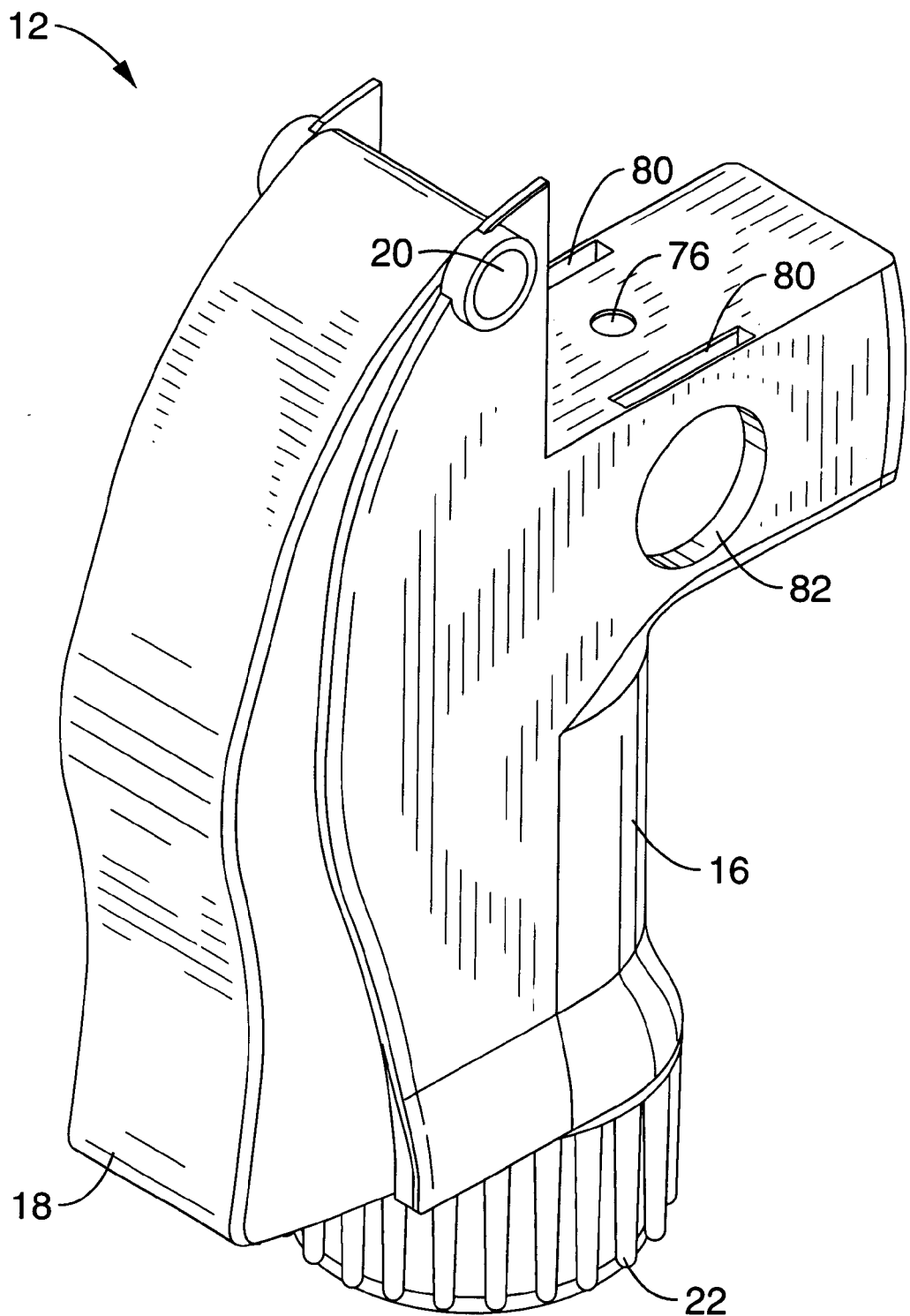
FIG. 4 is a perspective view of the actuator portion of the inhaler of FIG. 1.
Figure 5:
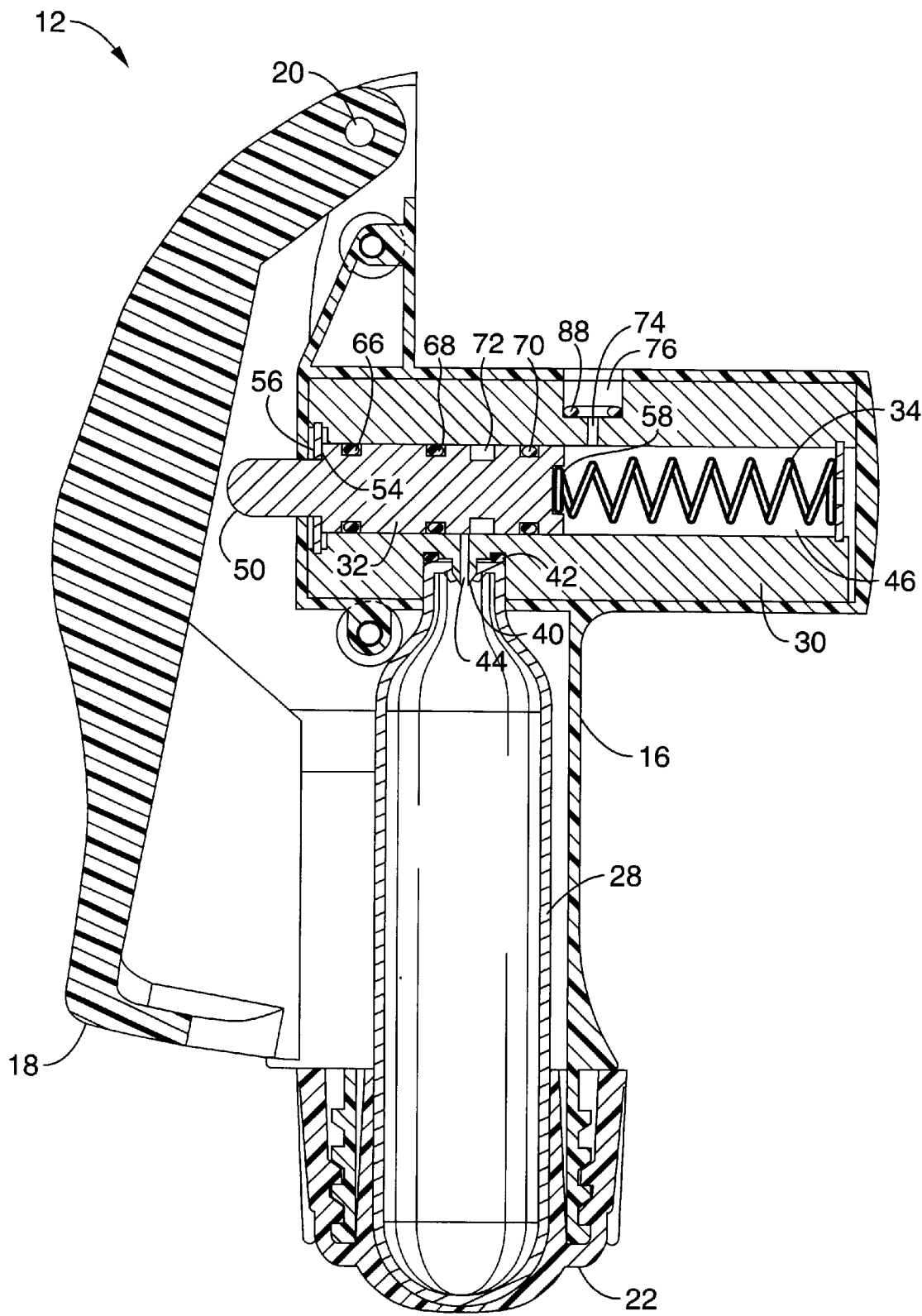
FIG. 5 is a side view in cross-section of the actuator of FIG. 4.
Figure 6:
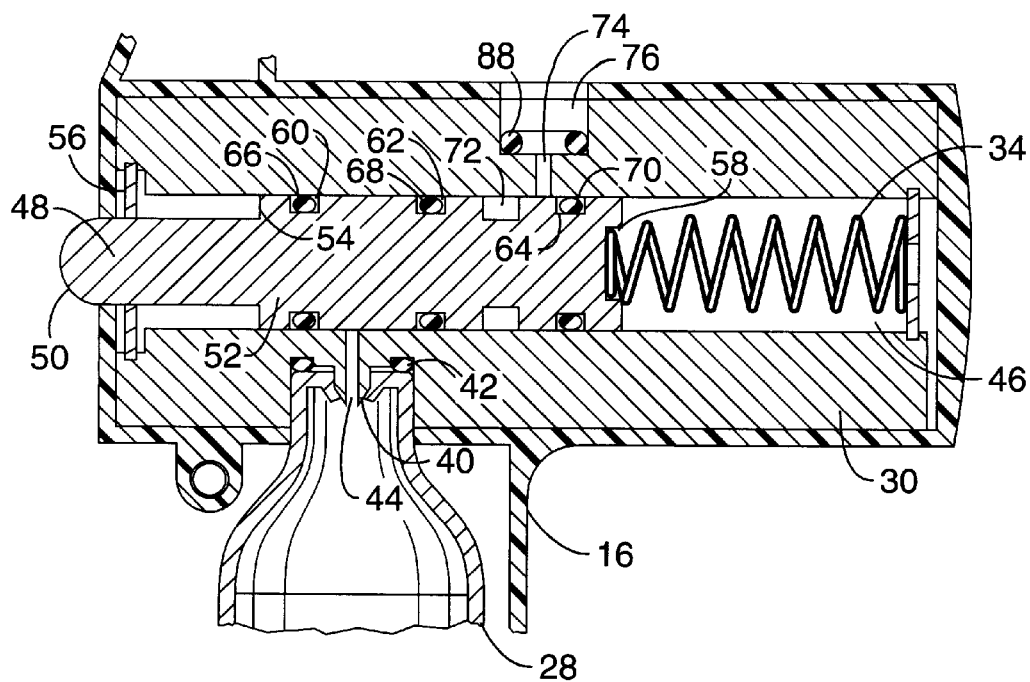
FIG. 6 is a side view in cross-section showing the valve portion of the actuator of FIG. 4 in the actuated state.
Figure 7:
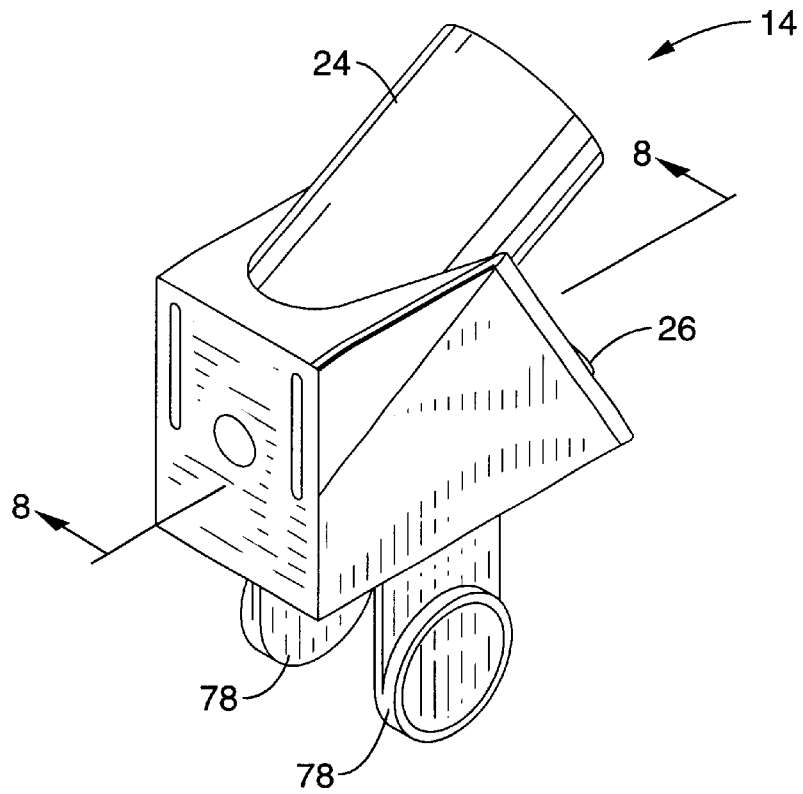
FIG. 7 is a perspective view of the aerosol generator portion of the inhaler of FIG. 1.
Figure 8:
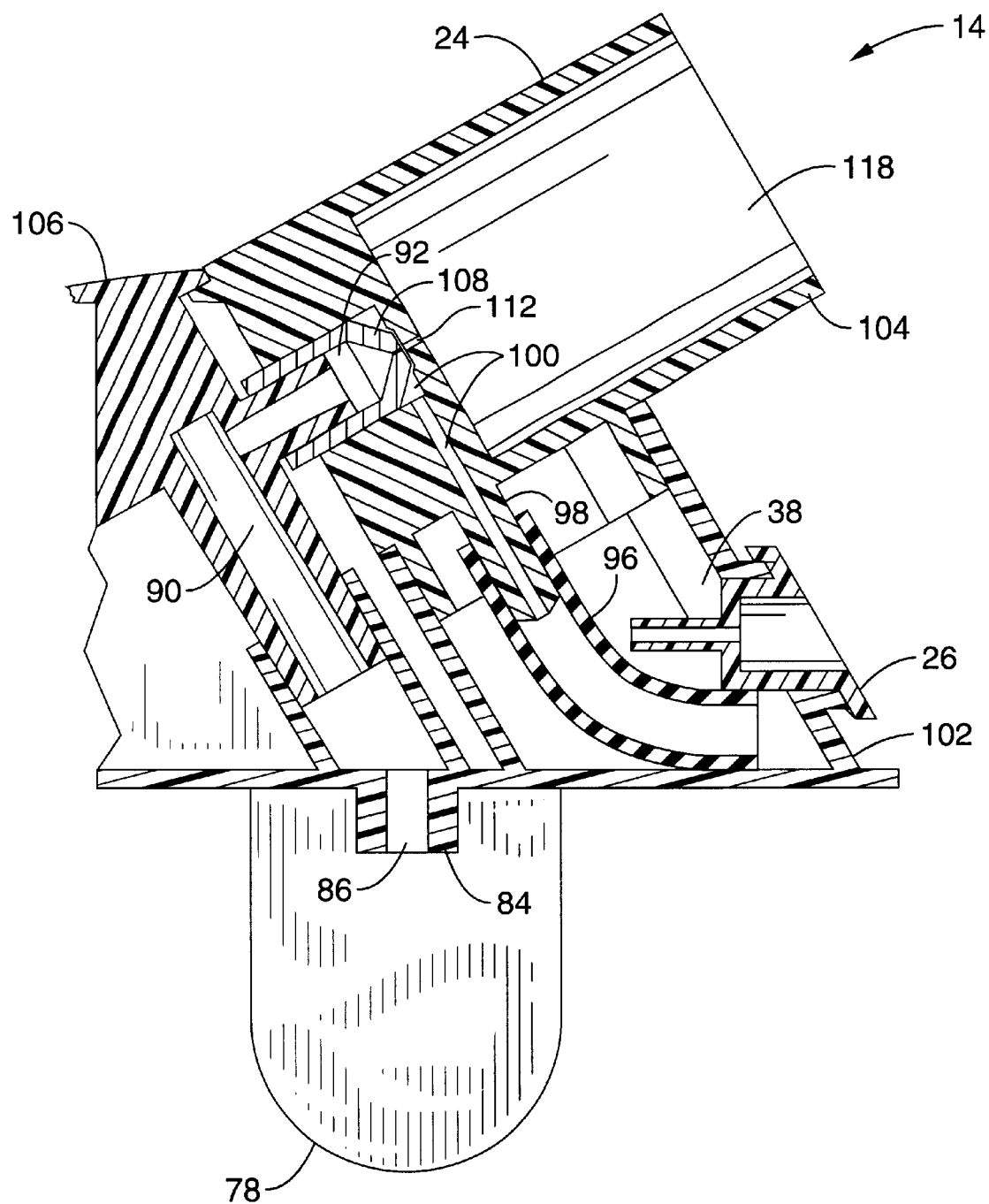
FIG. 8 is a side view in cross-section of the aerosol generator of FIG. 7.

As shown in FIG. 1, FIG. 2, and FIG. 3, aerosol generator 14 is caused to mate with actuator 12. As seen in FIG. 7 and FIG. 8, aerosol generator 14 has a pair of locking tabs 78 that pass through corresponding tab slots 80 and snap into tab receptacles 82, as shown in FIG. 4. When locking tabs 78 on aerosol generator 14 are fitted into tab receptacles 82 of actuator 12, inlet stem 84 of FIG. 8 is configured to fit to valve exit port 76 of actuator 12 as seen in FIG. 4, FIG. 5, and FIG. 6. Inlet stem 84 is mated with valve exit port 76 of actuator 12 such that sealing is established between the base of inlet stem 84 and actuator outlet o-ring 88 of FIG. 6. This allows for fluid communication between valve exit port 76 of actuator 12 and inlet stem 84 of aerosol generator 14 via valve exit conduit 74 of FIG. 6 and supply inlet 86 of FIG. 8.

Referring now to FIG. 8, it can be seen that compressed gas from the actuator 12 passes through supply inlet 86 of inlet stem 84 into supply channel 90 and into insert supply cavity 92 and out of the aerosolization nozzle 36 through jet orifice 94.

Figure 9:
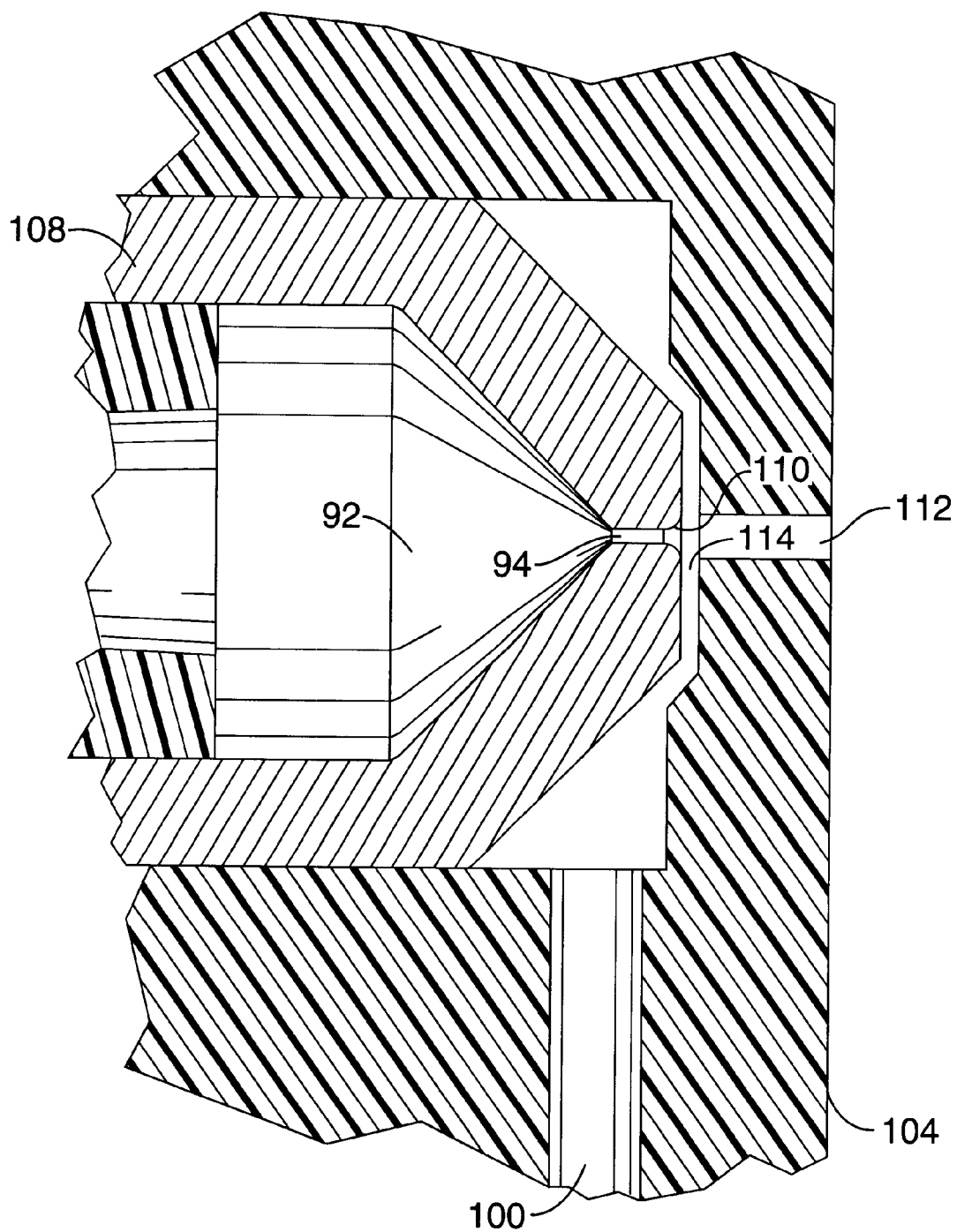
FIG. 9 is a detail side view in cross-section view of the nozzle portion of the aerosol generator of FIG. 7.

In the embodiment shown, reservoir 38 of aerosol generator 14 preferably has a liquid feed tube 96 mounted to liquid feed stem 98 that has a medicine channel 100 that is in fluid communication with the aerosolization assembly 36 as seen in FIG. 8 and FIG. 9. Thus, liquid entrained for aerosolization is caused to travel up liquid feed tube 98, medicine channel 100 of liquid feed stem 98 and directly to the nozzle section of the aerosolization nozzle 36, which is shown in the blown up view of FIG. 9.

In one embodiment, aerosol generator 14 is made of reservoir base 102, mouthpiece 104, elbow 106 and nozzle insert 108 components. In this embodiment, the aerosol generator 14 is assembled by placing liquid feed tube 96 on liquid feed stem 98 of mouthpiece component 104. Insert 108 is placed into the back of mouthpiece 104 creating the critical nozzle geometry shown in FIG. 9 where aerosolization occurs. Elbow 106 is placed into backside of insert 108 and then the assembly consisting of mouthpiece 104, insert 108 and elbow 106 are coupled with reservoir base 102. Plug 26 is then placed into reservoir component 102. Bonding between mating pieces may be established using press fits, adhesive techniques, or ultrasonic welding, except for mating between plug 26 and reservoir base 102, which is intended to be a sliding fit.

Liquid medication intended for aerosolization is placed in reservoir 38 by removing plug 26 and placing the medication directly into the liquid storage cavity of reservoir 38. Various liquid medications may be placed in the reservoir, as desired. In one embodiment, the liquid storage cavity of reservoir 38, contains a total volume of at least twice the intended liquid volume to be dispensed. This allows for the prevention of spilling of the contents of the liquid storage cavity of reservoir 38 and for different orientations of the aerosol generator 14.

An alternative to having a reservoir 38 for storing of medication for multiple doses, as above described, is to have means by which one dose may be made available to the aerosolization nozzle 36 at a given time. This would be the preferred embodiment of the current invention for medication requiring very strict output control or which requires special handling and storing, such as refrigeration. Strict output control would be realized because the aerosolization assembly 36 is designed so that it always attempts to entrain more liquid than there is present in the single dose reservoir. In this way, output is controlled solely by what is in the reservoir and not the critical dimensions of the aerosolization assembly 36 or the contents of carbon dioxide canister 28.

There exists many ways to have single dose reservoirs, including a very small version of the previously described liquid storage cavity 38, single ampules, or blister packs. A single dose may also include multiple puffs until the medication in the reservoir or ampule is depleted. In the case of ampules or blister pack cells, the liquid feed tube 96 would preferably be made from stiff plastic and would puncture the ampule or blister pack cell when entrainment was desired. After actuation, the empty ampule would be discarded, or, in the case of the blister pack, the liquid feed tube 96 would be advanced to the next blister pack cell when another dose of aerosol was required.

Still referring to FIG. 8, carbon dioxide gas supplied to supply inlet 86, is caused to pass up supply conduit 90 and into insert supply cavity 92. Referring also to FIG. 9, pressurized carbon dioxide gas that is provided to insert supply cavity 92 is caused to pass into jet orifice 94 with exit plane radius 110. In the preferred embodiment, jet orifice 94 has a diameter ranging from approximately 0.008 inches to approximately 0.016 inches, and exit plane radius 110 preferably has a diameter ranging from approximately 0.010 inches to approximately 0.020 inches. Because the supply pressure of the carbon dioxide canister is normally 750 psig, the jet formed in the jet orifice 94 will go supersonic. The jet will remain supersonic until such time that the cross sectional area of the exit area, due to exit plane radius 110, becomes too large, at which point the jet will be over expanded and reflected shock waves will form in the jet as shown graphically in FIG. 11 and schematically in FIG. 12. The diamond-shaped patterns of FIG. 11 and FIG. 12 show the shock wave patterns in the jet.

In the preferred embodiment of the present invention, exit plane radius 110 is large enough to insure that the supersonic jet formed from jet orifice 94 is over expanded. This will cause the first series of reflected shock waves to be compression shock waves and not expansion shock waves. Although expansion shock waves are capable of aerosolization, compression shock waves are preferable and considered slightly more optimum.

In an alternative configuration in which reflected expansion waves are desired initially, exit plane radius 110 would be made small enough, removed, or replaced with an appropriate taper, so that the exiting supersonic jet from jet orifice 94 was under expanded.

The supersonic jet exiting the jet orifice 94 and associated exit plane radius 110 will travel axially down shock chamber 112 and into the confines of mouthpiece 24. In the preferred embodiment, shock chamber 112 has a diameter ranging from approximately 0.020 inches to approximately 0.030 inches, or two to three times the diameter of the jet orifice 94. The resulting reflecting shock waves will continue along with the jet well outside the exit plane of shock chamber 112.

Optimally, interstitial space 114 has a gap distance between the exit plane and jet orifice 94 and the inlet of shock chamber 112 of between approximately 0.007 inches and 0.016 inches.

Referring also to FIG. 11 and FIG. 12, upon the initial formation of the supersonic jet, a vacuum will be created in interstitial space 114, which is in fluid communication with the medicine channel 100, thus causing liquid medication to be entrained from reservoir 38 through liquid feed tube 96, stem 98, channel 100 and introduced into shock chamber 112. The initial liquid entrained into shock chamber 112 comes in contact with the supersonic jet and the chain of reflected shock waves emanating from jet orifice 94. Upon contact with the shock waves and the jet, the initial liquid is agitated violently by the large shear forces produced by the shock waves and the discrepancy between the high velocity of the jet and the slow velocity of the liquid, which produces a tremendous burst of aerosol. The aerosol burst is carried out of the shock chamber 112 along with the expelled gas to mouthpiece 24. Subsequent to the initial fluid being introduced to shock chamber 112, the integrity of supersonic jet and resulting shock waves are destroyed due to the ongoing entrainment of more liquid, although shock waves are still present immediately proximal to the exit plane of jet orifice 94 and exit plane radius 110. These remaining shock waves are insufficient for the same production rate of aerosol produced initially due to the smaller exposed area and the location of the waves with respect to ongoing entrainment of liquid.

Accordingly, the charging volume 72 is preferably made large enough so as to deliver enough carbon dioxide gas to give the jet time to form, entrain liquid, and create the desired burst of aerosol. Once the carbon dioxide that is delivered from charging volume 72 to the jet orifice 94 is depleted, the jet ceases to exist all together, and no more liquid is entrained.

Referring back to FIG. 8, the aerosol exiting shock chamber 112 is carried into the internal cavity 118 of mouthpiece 24 where it is available for immediate inhalation by the patient. Referring also to FIG. 10, which is a view of aerosol generator 14 looking directly down the internal cavity 118 of mouthpiece 24, the backside of the internal cavity 118 of mouthpiece 24 is preferably equipped with four entrainment ducts 116, which allow ambient air to be entrained when the patient inhales. The diameter of the mouthpiece internal cavity 118 and the cross-sectional area of the four entrainment ports 116 are the primary means of controlling the geometry and speed of escaping aerosol 120 from shock chamber 112.

The length of the mouthpiece 24 and its internal cavity 118 also plays a role in the speed of escaping aerosol. Accordingly, the length of mouthpiece 24 is reduced to a minimum to prevent as much waste of aerosolized medication 120 as possible. In the current preferred embodiment, the mouthpiece internal cavity 118 has a diameter of approximately 0.775 inches and the preferred cross-sectional area of the four entrainment ducts 116 is approximately 0.08 inches squared or 0.02 inches square for each duct 116. Reducing the cross-sectional area of the four entrainment ducts 116 has been shown to reduce the exit velocity of the resulting aerosol if desired. Additionally, spacers and valve holding chambers are well known in the industry and can be connected directly to the outer diameter of mouthpiece 24.

Referring now to FIG. 13 through FIG. 30, an alternative embodiment of the invention is shown. As shown in FIG. 13, this embodiment comprises three principal parts: a reusable actuator handle 200, a disposable aerosol generator 202 and a disposable carbon dioxide cartridge assembly 204.

Turning now to FIG. 14 and FIG. 15 the carbon dioxide cartridge assembly 204 can be seen. The cartridge assembly 204 comprises a carbon dioxide canister 206 and gas canister cap 208. The carbon dioxide gas canister 206 includes a top 210 with threads 268 that is configured to engage with corresponding threads 266 within a valve assembly contained in actuator handle 200 as seen in FIG. 14 and FIG. 20.

Carbon dioxide represents only one of many different types of gases that can be used to power the current invention. Although carbon dioxide gas is preferred, it will be understood that any appropriate pressurized gas can be used. In one embodiment, gas canister 206 is bonded to the gas canister cap 208 with an adhesive and is designed with a large diameter to allow for sufficient torque during insertion of the carbon dioxide cartridge 206 into actuator handle 200. Carbon dioxide cartridge 206 preferably fits longitudinally into the underside of actuator handle 200 through cartridge port 212.

Turning now to FIG. 16 through FIG. 19, the preferred components of the actuator handle 200 are shown. Actuator handle 200 has an elongate actuator body 214 with cartridge port 212 at the bottom end. The actuator handle also includes a valve assembly 216, valve stem cover 218, trigger 220, and trigger pivot pin 222 as seen in FIG. 17.

Valve stem cover 218 has a pair of valve stem cover bosses 224 that engage angled edges 226 of trigger 220 such that when trigger 220 pivots about pin 222 the valve stem cover 218 moves longitudinally within handle body 214. Accordingly, when assembled, valve stem cover 218 mates with valve assembly 216 and the bosses 224 engage with trigger 220 such that when trigger 220 is squeezed, trigger cam surface 226 engages with valve stem bosses 224 such that valve stem cover 218 is forced to move downward causing valve assembly 216 to become actuated as described herein.

Referring now to FIG. 18, FIG. 19 and FIG. 20, the components of the preferred valve assembly are shown. Valve assembly 216 has a generally cylindrical body 228 that is configured to fit within actuator handle 200 as seen in FIG. 17 and FIG. 18. In one embodiment, valve assembly body 216 has one of more raised rails 230 on the outer surface that slide within corresponding slots in the interior of the handle 200 (not shown) as well as slots 232 in valve stem cover 218. The raised rail 230 and slot configuration securely positions the valve assembly and eliminates any rotational motion of the valve assembly 216 when the threads 268 of the top 210 of gas canister 206 are screwed into the threads 268 of the valve assembly. Rails 230 also facilitate the linear movement of the valve stem cover 218 with respect to the valve assembly 216 when the trigger 220 is pressed.

Referring now to the exploded view of the valve assembly 216 in FIG. 19 and the cross sectional view of FIG. 20, the regulation of the flow of gas from the canister 206 through the stem exit port 236 can be seen. In the embodiment shown in FIG. 19, the valve assembly 216 has a canister seal 238, valve body 228, hollow canister puncture pin 240, puncture pin valve seal 242, valve spacer 244, central valve seal 246, cylinder 248 with chamber 250, stem plug 260, valve stem 234, top valve seal 252, and end plate 254. The exploded view in FIG. 19 shows the relative position of each of these components. The cross sectional schematic view in FIG. 20 shows the relative position of the components when assembled.

Figure 19:
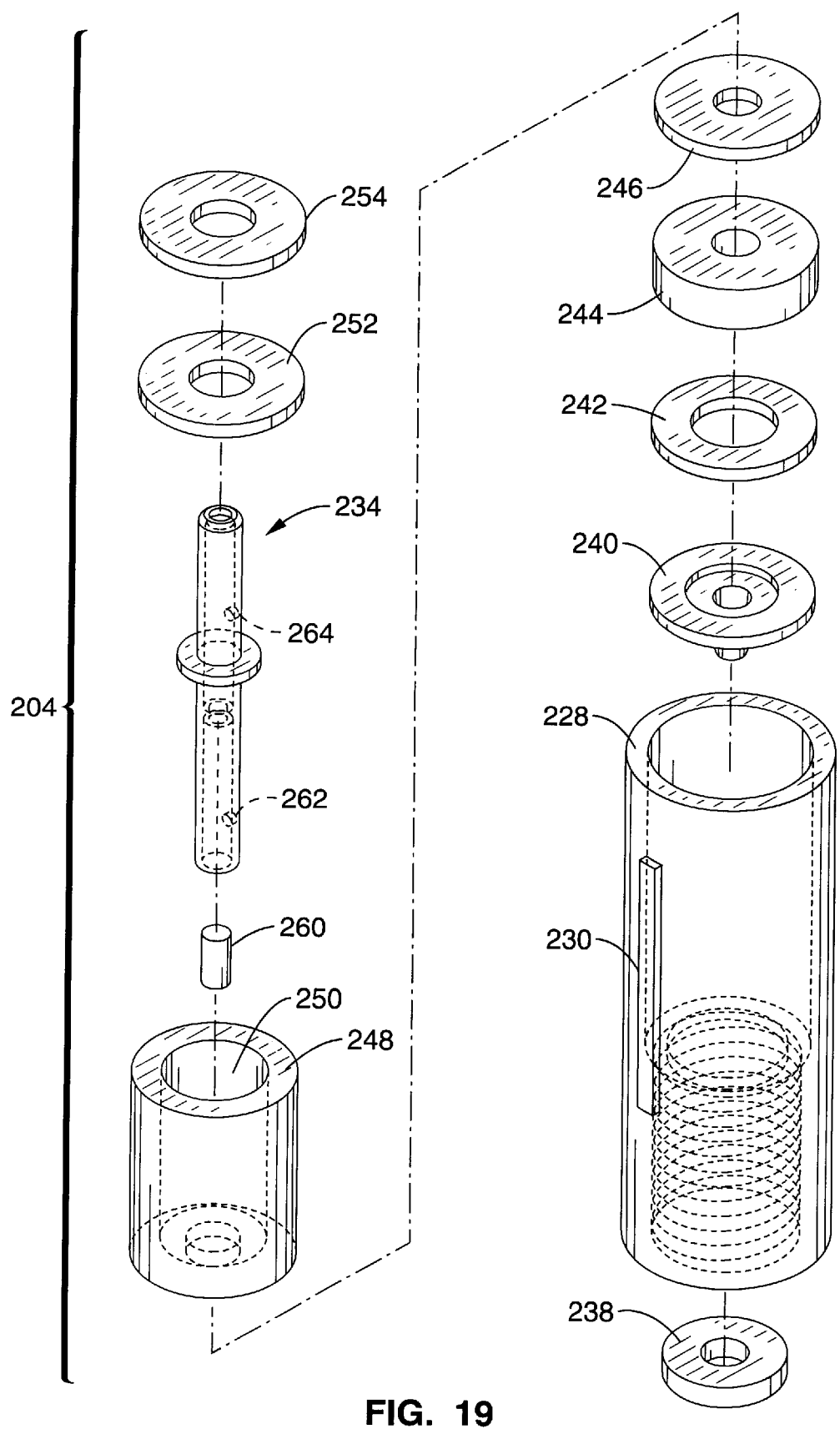
FIG. 19 is a exploded view of the valve of FIG. 18.

Seals 238, 242, 246 and 252 as well as stem plug 260 are preferably made of urethane, due to the resistance of this material to compressed carbon dioxide. Valve spacer 244 and cylinder 248 are preferably made of injected molded nylon. Valve body 228, canister puncture pin 240, valve stem 234, and end plate 234 are preferably made of machined aluminum but may also be made of glass-reinforced nylon. In the embodiment shown, the parts are assembled as shown in FIG. 19 and then valve body end 256 is rolled over in a machining operation to keep the parts in place.

Figure 20:
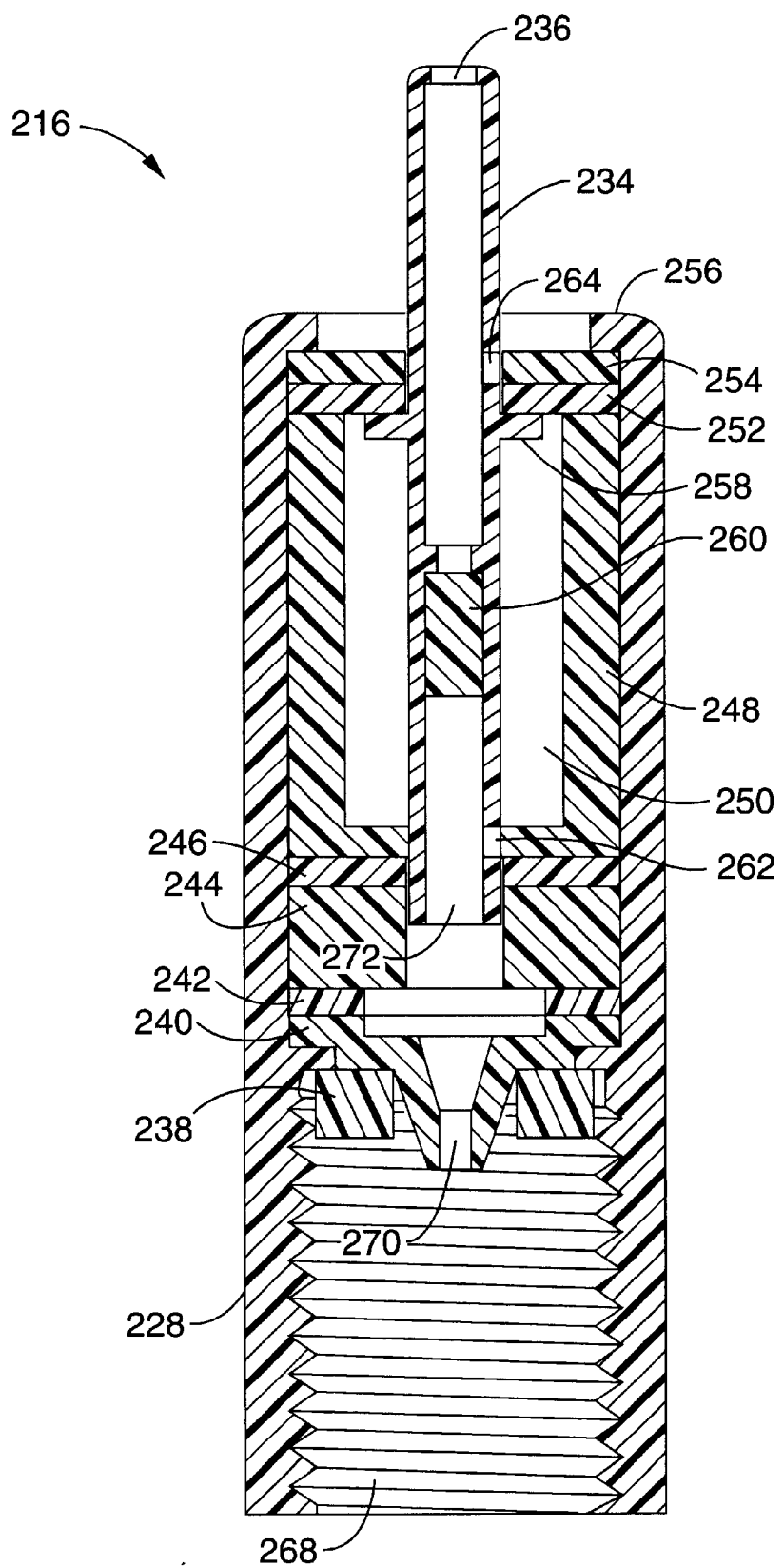
FIG. 20 is a side view in cross-section view of the valve of FIG. 18.
Figure 21:
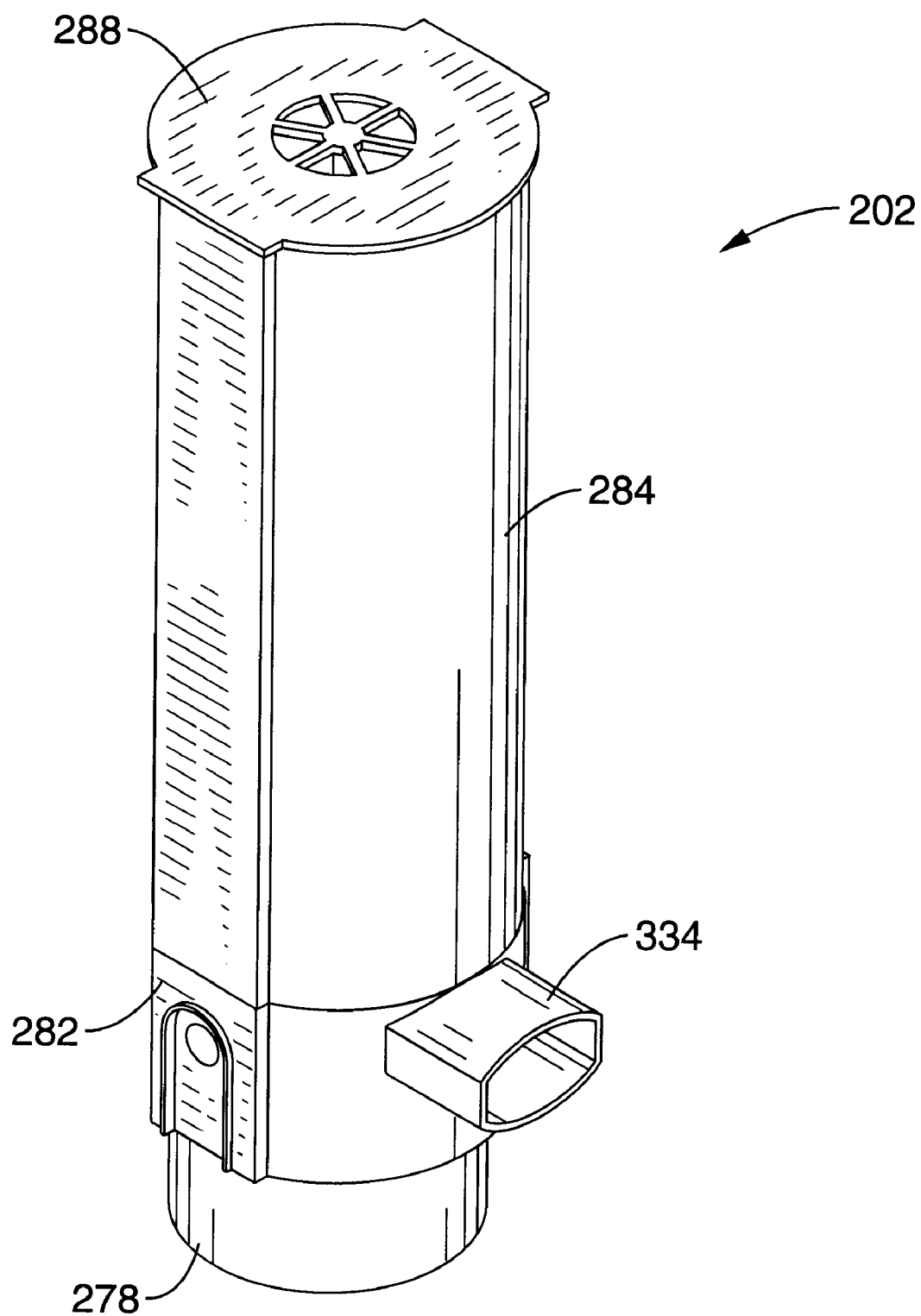
FIG. 21 is a perspective view of the disposable inhaler aerosol generator portion of the inhaler of FIG. 13.
Figure 22:
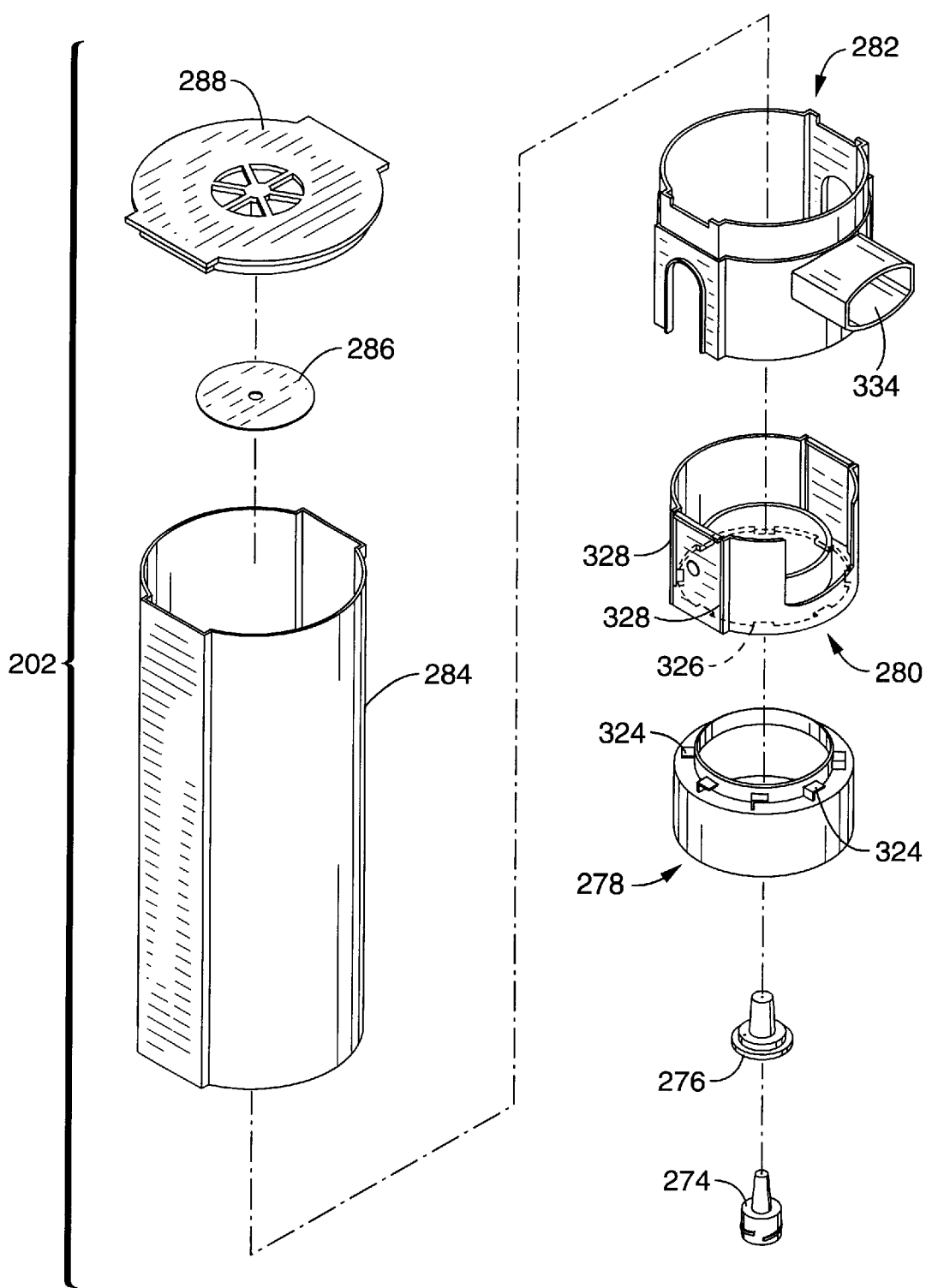
FIG. 22 is a exploded view of the aerosol generator of FIG. 21.
Figure 23:
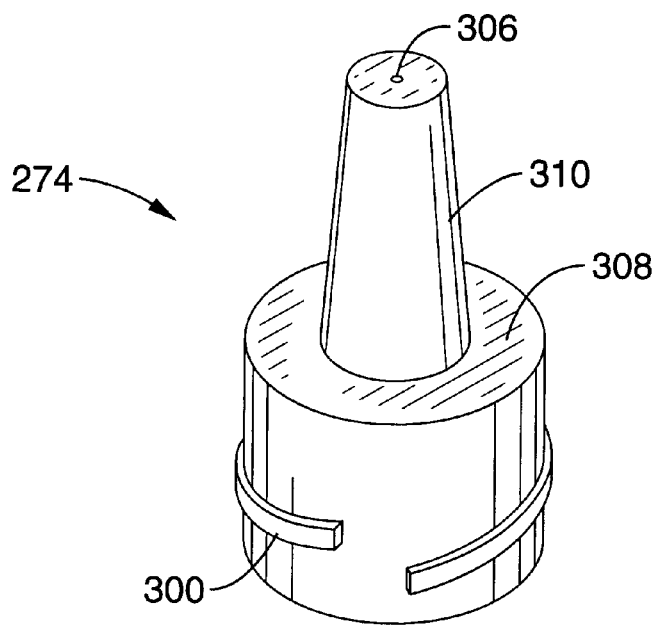
FIG. 23 is a top view of the jet employed in the inhaler of FIG. 13.
Figure 24:
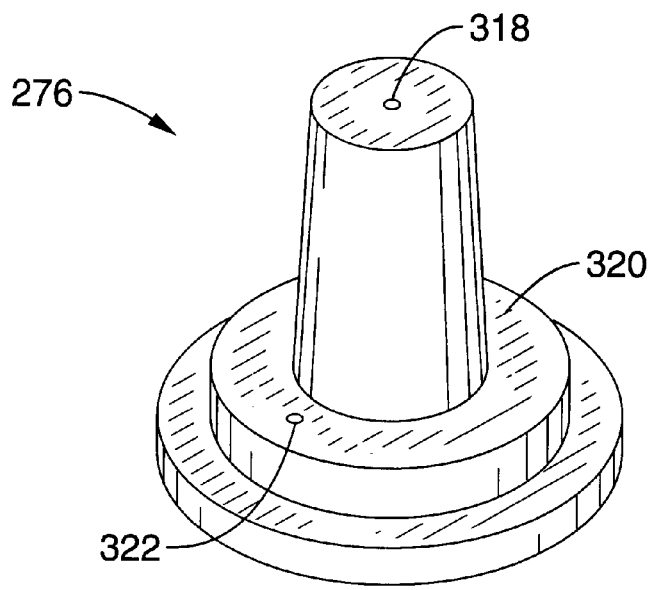
FIG. 24 is a top view of the secondary employed the inhaler of FIG. 13.
Figure 25:
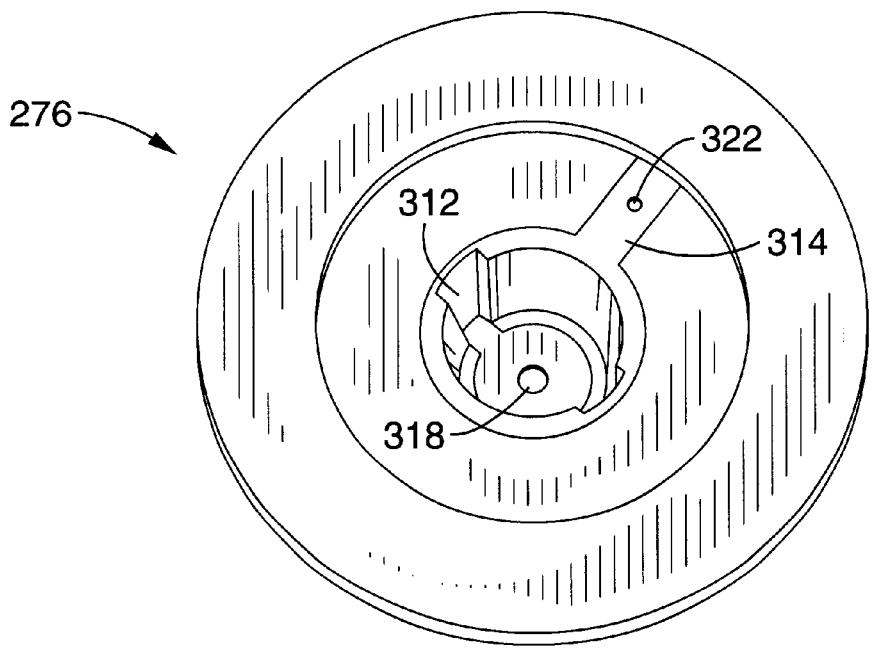
FIG. 25 is a bottom view of the secondary of FIG. 24.
Figure 26:
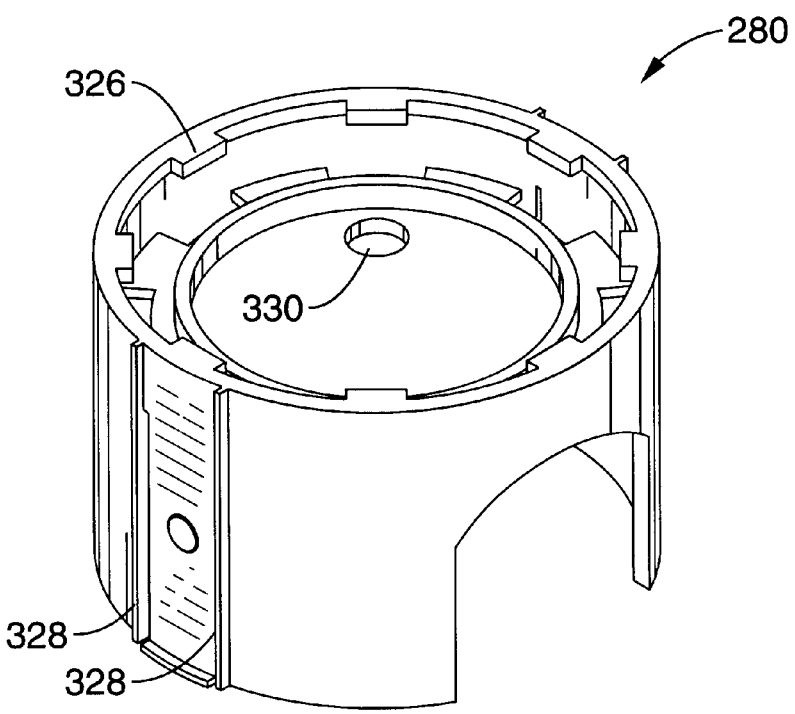
FIG. 26 is a perspective view of the cap employed in the inhaler of FIG. 13.
Figure 27:
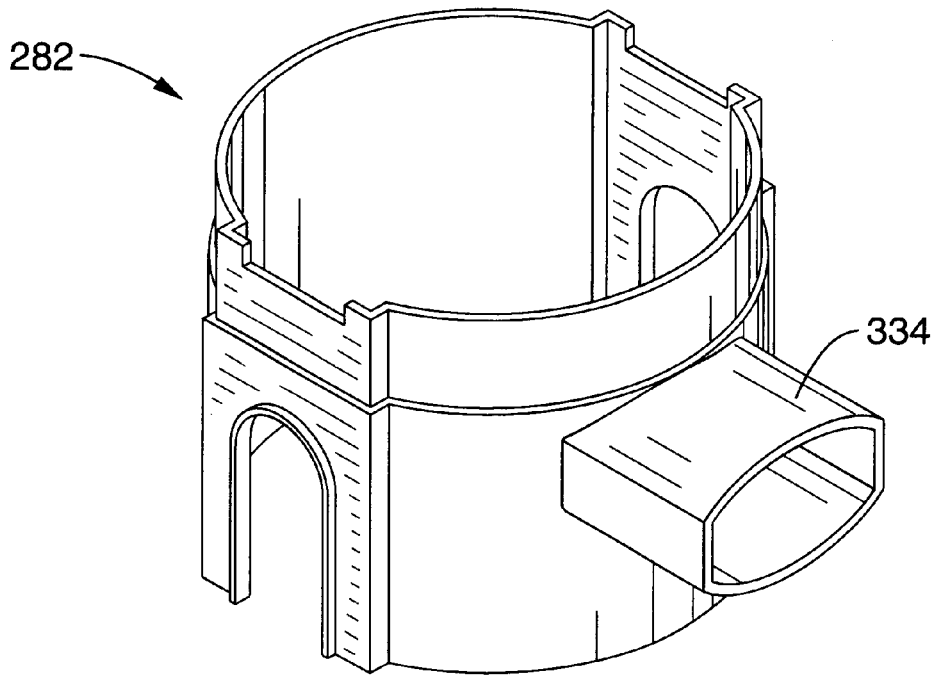
FIG. 27 is a perspective view of the column base employed in the inhaler of FIG. 13.
Figure 28:
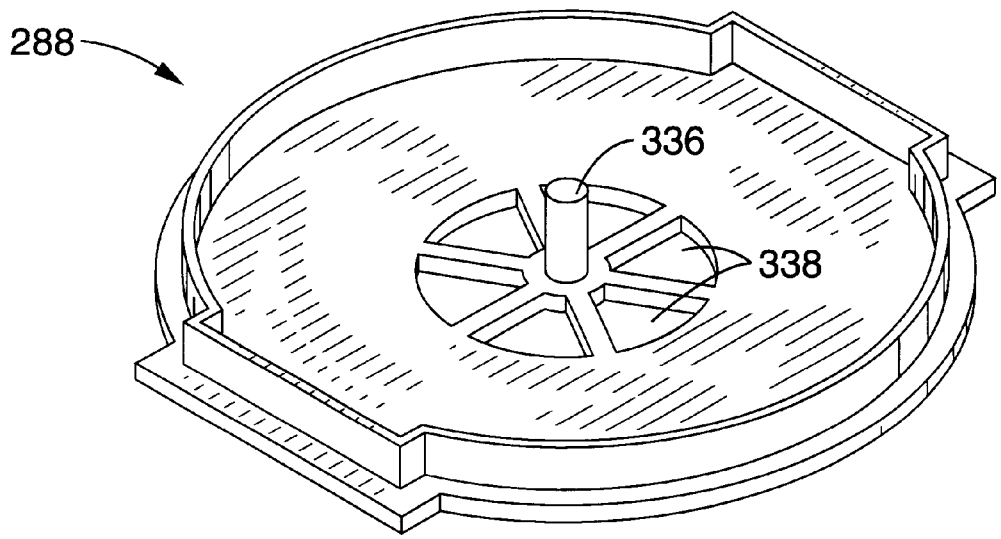
FIG. 28 is a perspective view of the end of the column of FIG. 27.

Referring now to FIG. 20, the regulation of the gas flow and the movements of the valve components of one embodiment of the valve assembly can be seen. Valve stem 234 can move axially within chamber 250 of cylinder 248. A circumferential flange 258 on stem 234 stops the outward movement of stem 234 by engaging the interior side of the top valve seal 252. Valve stem 234 is tubular and has a plug 260 in the approximate center of the stem. In addition, stem 234 has a valve stem inlet orifice 262 and a valve stem exit orifice 264 that communicate from the interior of the stem 234 to the exterior.

When the top 210 of carbon dioxide canister 206, for example, is advanced on threads 266 of the valve assembly body 228, the top of canister 206 will engage hollow puncture pin 240, which pierces the top 206. The top 210 of carbon dioxide canister 206 is caused to seat against canister seal 238 as the threads 269 of canister 206 are advanced along the threads 266 of the valve body.

Once seated, carbon dioxide becomes available to valve assembly 216 through canister puncture pin orifice 270. The valve assembly 216 in the normally closed position is shown in FIG. 20. In this position, valve stem 234 is pushed by the pressure of the compressed carbon dioxide gas so that valve stem flange 258 is caused to seal against the upper valve seal 252.

In the closed position, carbon dioxide is allowed to pass from the canister 206 through orifice 270, valve seal 242 and valve spacer 244 to valve stem inlet port 272 located at the proximal end of stem 234. Gas within stem 234 must exit the stem through inlet orifice 262 because of plug 252 to fill the chamber 250 of cylinder 248 that exists between the outer diameter of valve stem 234 and the inner diameter of valve cylinder 248. Valve seals 246 and 252 are sized on the internal diameters to fit and seal against the outer diameter of valve stem 234. In the closed position, chamber 250 ultimately becomes filled with carbon dioxide gas to the same pressure as that of canister 206.

In the open position, valve stem 234 is moved in an axial direction, against the force of internal pressure, toward the canister 206. It will be seen that when stem 234 is moved axially, valve stem inlet orifice 262 is caused to pass by central valve seal 246 thereby disconnecting fluid communication between the carbon dioxide pressure provided by the carbon dioxide cartridge 206 and interstitial space of chamber 250. Further axial motion of valve stem 234 causes valve stem exit orifice 264 to pass through top valve seal 252 allowing the compressed gas in chamber 250 to exit the chamber through stem exit orifice 264 to the interior of valve stem 234 and out through valve stem exit port 236. In the preferred embodiment, the volume of gas that is discharged through stem exit port 236 is predictable and consistent for each actuation and is determined by the relative internal volumes of jet 274 and the volume of chamber 243. When the stem 234 is returned to the normally closed position, the chamber 250 refills and becomes ready for the next actuation.

Turning now to FIG. 21 through FIGS. 28, 31 and 32, the preferred aerosol generator component of the present invention is described. As seen in the exploded view of FIG. 22, the preferred aerosol generator 202 comprises a jet 274, secondary 276, reservoir cup 278, cap 280, column base 282, column 284, flapper valve 286, and column end 288.

The jet 274, shown in FIG. 23, has a set of external threads 300 that allow the aerosol generator 202 to fit onto actuator handle 200 through the engagement of threads 300 with the corresponding threads 302 of valve stem cover 218 as shown in FIG. 16. The distal end of valve stem 234 mates with the inside diameter of valve stem cover 218 to provide an adequate seal. The interior of jet 273 is configured to receive valve stem cover exit port 304 when the external threads 300 of jet 274 is coupled with the valve stem cover 218. Jet 274 also has a jet orifice 306 that allows the flow of gas received from exit port 236 from valve stem 234 through valve stem cover exit port 304.

Jet 274 and the secondary 276 shown in FIG. 24 interlock together such that the external surfaces 308, 310 of jet 274 and the internal surfaces of secondary channels 312, 314 of secondary 276, seen in FIG. 25, to form interstitial fluid passages 316.

Secondary 276, shown in FIG. 24 and FIG. 25 also has an opening 318 that operates as a shock chamber. As in the previously described embodiment, jet orifice 306 mates with secondary 276 such that the shock chamber 318 and jet orifice 306 are aligned to form the shock wave aerosolization nozzle, and preferably have the same nozzle dimensions as described in the first embodiment.

Secondary 276 fits into the bottom of reservoir cup 278 to form a reservoir for the holding of liquid medication such that secondary surface 320, shown in FIG. 24, preferably becomes the lowest point of the liquid reservoir. Penetrating through surface 320 through to secondary channel 314 is liquid choke orifice 322. Liquid choke orifice 322 provides further means, through the resistance of the flow of liquid, for limiting the rate and amount of liquid entrained by the shock wave aerosolization nozzle. The preferred optimum size range for liquid choke orifice 322 is less than approximately 0.050 inches.

Reservoir cup 278 mates with cap 280 through the engagement of locking clips 324 on reservoir cup 278 shown in FIG. 22 with locking members 326 as shown in FIG. 26. Reservoir cup 278 and cap 280 are designed to allow the exit plane of secondary 276 to protrude through a bore 330 in cap 280 allowing for aerosol entry directly into aerosol chamber 340, while creating at the same time anti-spill ability for reservoir 332 as shown in FIG. 30. Anti-spill reservoir volume 332, shown in FIG. 30 is designed such that when invention is tipped sideways or upside down, liquid in reservoir does not spill out.

As seen in FIG. 26, cap 280 is preferably equipped with two pairs of protruding ribs 328 located on opposite sides of the cap which allow for column base 282 and spacer column 284 to slide over cap 280 without rotating.

Column base 282, shown in FIG. 27, is equipped with mouthpiece 334 to allow for patient inhalation. Column 284 is preferably tubular and configured to fit onto column base 282. Column base 282, column 284, and column end 288 are preferably all made of anti-static plastic material to prevent the loss of charged aerosol particles due to the attraction of the particles to oppositely charged aerosol chamber surfaces.

Referring now to FIG. 22 and FIG. 28, flapper valve 286 is preferably a thin rubber circular piece that has a center hole which fits over flapper valve post 336 of column end 288. Flapper valve 286 preferably has a large enough outer diameter to encircle inhalation ports 338. Column end 288 fits onto column 284 to form an aerosolization chamber 340.

Once aerosol is produced from the jet 274 and shock chamber 318, it enters into the aerosolization chamber 340 of column 284 where it is stored until patient inhales on mouthpiece 334. Flapper valve 286 prevents the patient from forcing stored aerosol out of chamber with an accidental exhalation. Upon inhalation, flapper valve 286 allows room air to be entrained into chamber 340.

Referring now to FIG. 29 and FIG. 30, the completed coupling of the aerosol generator 202, the actuator handle 200 and the gas canister assembly 204 can be seen. The apparatus can be conveniently stored in two pieces that are coupled prior to use.

Figure 31:
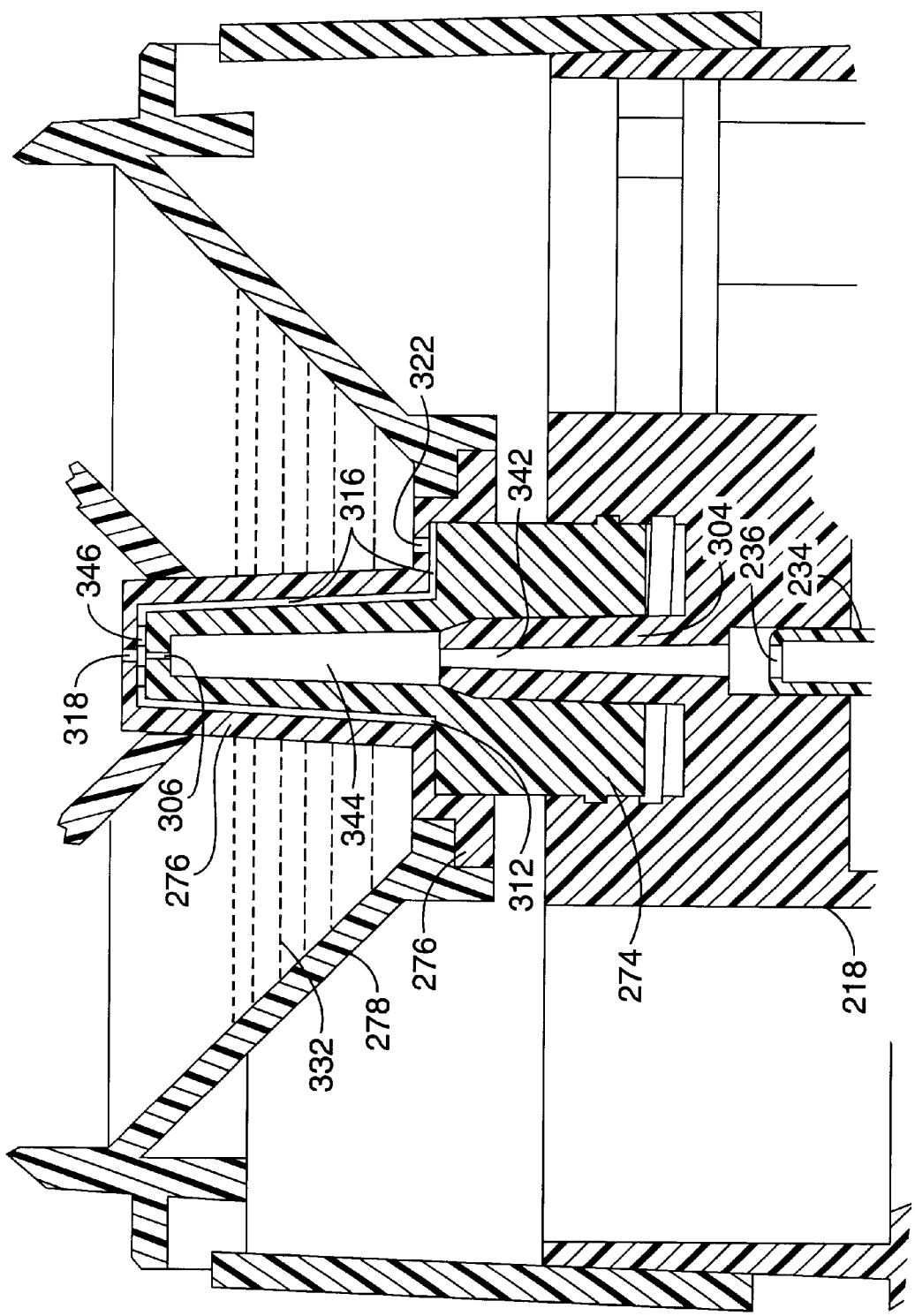
FIG. 31 is a detail side view in cross-section of the supersonic nozzle assembly portion of the inhaler of FIG. 13.
Figure 32:
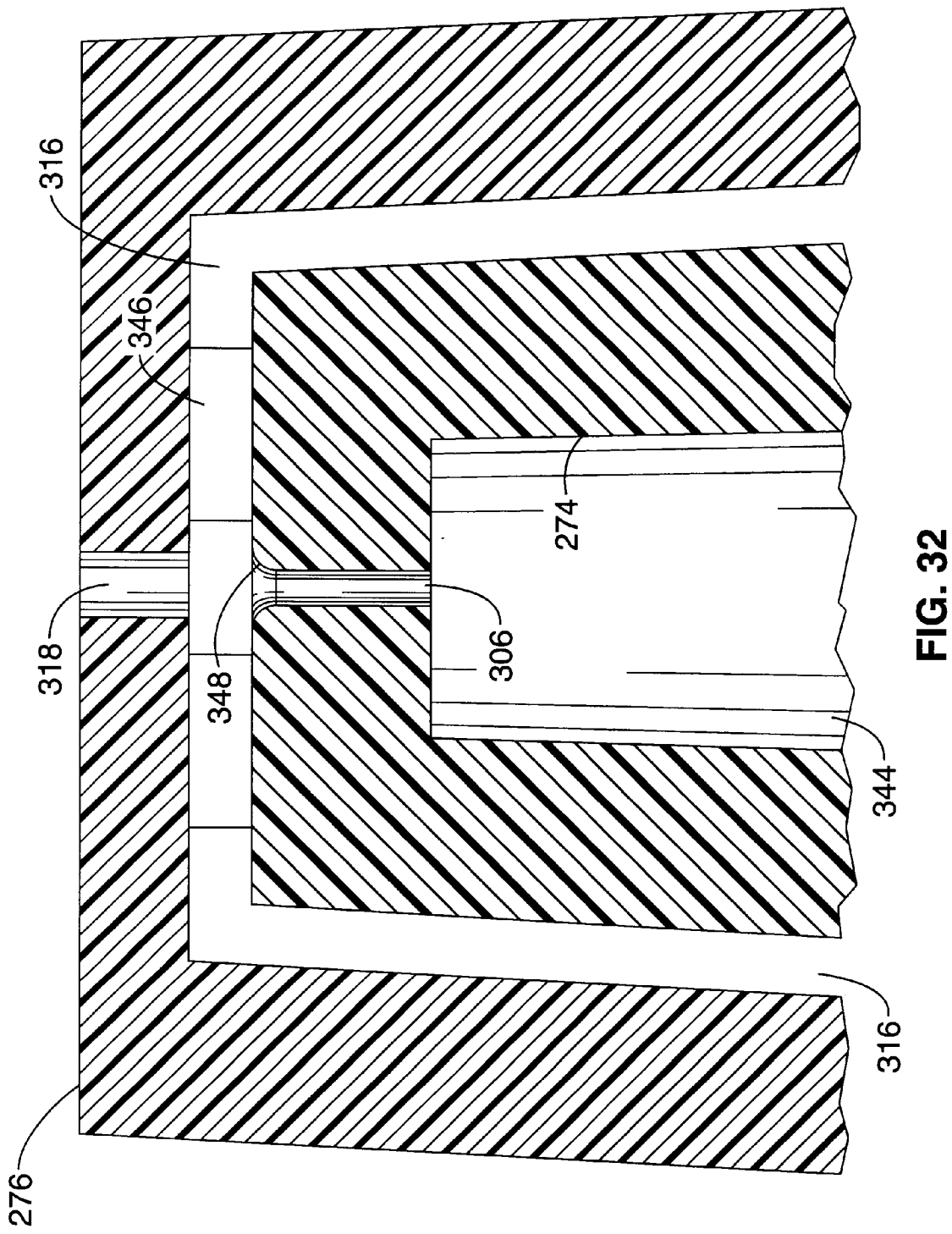
FIG. 32 is a detail side view in cross-section of the jet and shock chamber portion of the nozzle assembly of FIG. 31.
Figure 33:
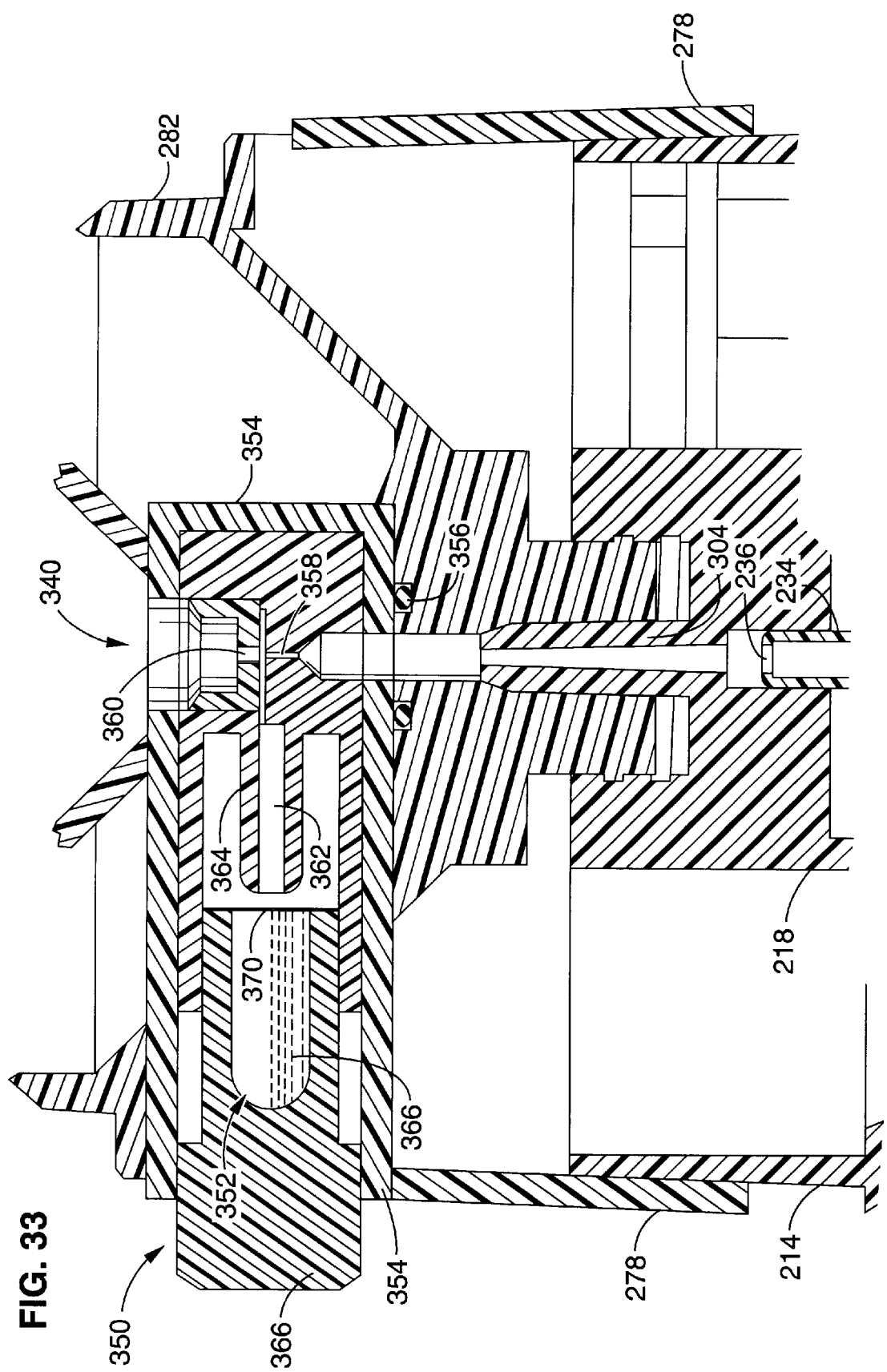
FIG. 33 is a side view in cross-section of an embodiment of an inhaler according to the present invention employing a disposable cartridge containing both the nozzle and a blister pack of medication.

Referring also to FIG. 31 and FIG. 32, the full structure of the preferred alternative embodiment of the apparatus can be seen. In use, gas from canister 206 that has been previously seated on canister seal 238, enters the valve assembly 216 through pin orifice 270. Gas enters chamber 250 through valve stem inlet port 272 and valve stem inlet orifice 262 until the pressure of the gas in chamber 250 is equal to the pressure of the gas in canister 206. Upon actuation of trigger 220 as previously described, the contents of chamber 250 exit through valve stem outlet orifice 264 and valve stem outlet port 236 as a burst of gas. The burst of gas travels through the internal conduit 342 of the valve stem cover 218, and into the interior 344 of jet 274. Jet orifice 306 is dimensioned so that the jet formed in the jet orifice 306 will be supersonic producing the aerosolization process as described in the first embodiment. Additionally, jet orifice 306, exit plane radius 348 and shock chamber 318 preferably have the same dimensions and performance characteristics as the first embodiment described herein.

Medicine held in reservoir 332 enters choke port 322 and channels 312 and is drawn to interstitial space 346 between the jet 274 and secondary 276 and aerosolized when brought in contact with the supersonic jet. The aerosolized medication is then contained in the interior chamber 340 of column 284 for inhalation by the patient.

In accordance with a still further embodiment of the invention, as shown in FIG. 33, the equivalent of jet 274 and secondary 276, forming the supersonic shock nozzle assembly, can be enclosed in a small cartridge 350 along with a single blister pack 352 containing sufficient medication for one aerosol treatment. In this single use embodiment, the cartridge 350 is to be inserted into the base of the column 282 that is coupled to the body 214 of actuator handle 200 so as to cause the supersonic shock nozzle to become oriented above the channel 342 of valve cover port 304. Cartridge 350 has an exterior housing 354 that is configured to be disposed in a slot within the base 282 as needed by the patient. After insertion into the base, cartridge 350 is sealed to the outlet passage of carbon dioxide with o-ring 356.

The shock nozzle assembly has a jet orifice 358 and a shock chamber 360 that are preferably configured as described in the previous embodiments. Adjacent to jet orifice 358 is liquid feed line 362 that is in fluid communication with prong 364.

Simultaneous with insertion of the cartridge 350, the foil barrier 370 of blister pack 352 is preferably punctured by the prong 364 by pressing a button 368 and the medicine 366 within blister pack 352 is capable of being entrained from the blister pack 352 through liquid feed tube 362 and through to the supersonic shock nozzle. Aerosol is directed to chamber 340 from the supersonic shock nozzle for inhalation by the patient. Accordingly, as gas is caused to pass through the jet orifice 358 and shock chamber 360, the medicine 366 in the blister pack 352 is entrained and aerosolized by the supersonic shock nozzle as in the previous embodiment. Upon completion of the aerosol treatment, the supersonic shock nozzle/blister cartridge 350 may be removed and discarded by the user. This single use embodiment may work with or without an aerosol storage chamber and has the advantage of reducing possible contamination of the supersonic shock nozzle between treatments.

It can be seen, therefore, that the present invention provides an inhaler device that can deliver a burst of aerosol from an aqueous solution. In this way a number of advantages are realized which include, less expense on the part of the patient, less cost in formulation development, better aftertaste, portability, and convenience.

Although the description above contains many specificities, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An inhaler apparatus, comprising:
   a reservoir for containing compressed gas;
   a supersonic shock nozzle; and
   a user actuated valve configured to release said compressed gas in bursts for delivery to said supersonic shock nozzle;
   wherein said supersonic shock nozzle comprises
      a jet orifice configured to receive compressed gas from said reservoir, and
      a sonic shock chamber configured to receive compressed gas discharged from said jet orifice;
   wherein said jet orifice is configured to produce a supersonic jet from said compressed gas;
   wherein said shock chamber is configured to receive said supersonic jet and produce shock waves; and
   wherein if said supersonic jet is over expanded or under expanded, said supersonic jet will establish a series of reflected compression and expansion shock waves in said shock chamber.

2. An apparatus as recited in claim 1, wherein said supersonic jet will be approximately the diameter of the jet orifice and travel down the axis of the shock chamber.

3. An apparatus as recited in claim 1, wherein if said supersonic jet is perfectly expanded, a cylindrical shock wave will be generated in said shock chamber that envelopes the entire jet.

4. An apparatus as recited in claim 1, wherein upon formation of said supersonic jet and resulting shock waves in said shock chamber, a vacuum is generated which causes liquid from a liquid reservoir to be entrained through a liquid feed into said shock chamber.

5. An apparatus as recited in claim 4, wherein upon entrainment of liquid into the shock chamber, the initial liquid entrained comes in contact with shock waves, producing copious amounts of aerosol particles suitable for inhalation.

6. An apparatus as recited in claim 5, wherein once liquid has been entrained into the shock chamber and supersonic jet, the integrity of the supersonic jet and resulting reflecting shock waves is destroyed, resulting in less subsequent production of aerosol particles than the initial burst and generally a larger particle size.

7. An apparatus as recited in claim 1, further comprising:
a cartridge containing said supersonic shock nozzle and a blister pack containing medication for one aerosol treatment.

8. An apparatus as recited in claim 7, wherein said cartridge is disposable.

9. An apparatus as recited in claim 7, further comprising:
an actuator handle coupled to said actuator valve;
wherein said actuator handle is configured to receive said cartridge.

10. An apparatus as recited in claim 9, wherein insertion of said cartridge into said actuator handle causes said nozzle to be sealed with an outlet passage of said reservoir containing compressed gas upon actuation of the actuator handle.

11. An apparatus as recited in claim 9, wherein insertion of said cartridge into said actuator handle causes said blister pack to be punctured.

12. An apparatus as recited in claim 9, wherein medication in said blister pack is entrained and aerosolized by said nozzle upon actuation of said actuator handle.

13. An inhaler apparatus, comprising:
a reservoir for containing compressed gas;
a supersonic shock nozzle; and
a user actuated valve configured to release said compressed gas in bursts for delivery to said supersonic shock nozzle;
wherein said supersonic shock nozzle comprises
a jet orifice configured to receive compressed gas from said reservoir, and
a sonic shock chamber configured to receive compressed gas discharged from said jet orifice;
wherein said jet orifice is configured to produce a supersonic jet from said compressed gas;
wherein said shock chamber is configured to receive said supersonic jet and produce shock waves;
wherein upon formation of said supersonic jet and resulting shock waves in said shock chamber, a vacuum is generated which causes liquid from a liquid reservoir to be entrained through a liquid feed into said shock chamber;
wherein upon entrainment of liquid into the shock chamber, the initial liquid entrained comes in contact with shock waves, producing copious amounts of aerosol particles suitable for inhalation; and
wherein once liquid has been entrained into the shock chamber and supersonic jet, the integrity of the supersonic jet and resulting reflecting shock waves is destroyed, resulting in less subsequent production of aerosol particles than the initial burst and generally a larger particle size.

14. An apparatus as recited in claim 13, wherein if said supersonic jet is over expanded or under expanded, said supersonic jet will establish a series of reflected compression and expansion shock waves in said shock chamber.

15. An apparatus as recited in claim 14, wherein said supersonic jet will be approximately the diameter of the jet orifice and travel down the axis of the shock chamber.

16. An apparatus as recited in claim 13, wherein if said supersonic jet is perfectly expanded, a cylindrical shock wave will be generated in said shock chamber that envelopes the entire jet.

17. An apparatus as recited in claim 13, further comprising:
a cartridge containing said supersonic shock nozzle and a blister pack containing medication for one aerosol treatment.

18. An apparatus as recited in claim 17, wherein said cartridge is disposable.

19. An apparatus as recited in claim 17, further comprising:
an actuator handle coupled to said actuator valve;
wherein said actuator handle is configured to receive said cartridge.

20. An apparatus as recited in claim 19, wherein insertion of said cartridge into said actuator handle causes said nozzle to be sealed with an outlet passage of said reservoir containing compressed gas upon actuation of the actuator handle.

21. An apparatus as recited in claim 19, wherein insertion of said cartridge into said actuator handle causes said blister pack to be punctured.

22. An apparatus as recited in claim 19, wherein medication in said blister pack is entrained and aerosolized by said nozzle upon actuation of said actuator handle.

23. An inhaler apparatus, comprising:
a reservoir for containing compressed gas;
a jet orifice configured to receive compressed gas from said reservoir;
a sonic shock chamber configured to receive compressed gas discharged from said jet orifice; and
a user actuated valve configured to release said compressed gas in bursts for delivery to said supersonic shock nozzle;
wherein said jet orifice is configured to produce a supersonic jet from said compressed gas;
wherein said shock chamber is configured to receive said supersonic jet and produce shock waves; and
wherein if said supersonic jet is over expanded or under expanded, said supersonic jet will establish a series of reflected compression and expansion shock waves in said shock chamber.

24. An apparatus as recited in claim 23, wherein said supersonic jet will be approximately the diameter of the jet orifice and travel down the axis of the shock chamber.

25. An apparatus as recited in claim 23, wherein if said supersonic jet is perfectly expanded, a cylindrical shock wave will be generated in said shock chamber that envelopes the entire jet.

26. An apparatus as recited in claim 23, wherein upon formation of said supersonic jet and resulting shock waves in said shock chamber, a vacuum is generated which causes liquid from a liquid reservoir to be entrained through a liquid feed into said shock chamber.

27. An apparatus as recited in claim 26, wherein upon entrainment of liquid into the shock chamber, the initial liquid entrained comes in contact with shock waves, producing copious amounts of aerosol particles suitable for inhalation.

28. An apparatus as recited in claim 27, wherein once liquid has been entrained into the shock chamber and supersonic jet, the integrity of the supersonic jet and resulting reflecting shock waves is destroyed, resulting in less subsequent production of aerosol particles than the initial burst and generally a larger particle size.

29. An apparatus as recited in claim 23, further comprising:
  a cartridge containing said supersonic shock nozzle and a blister pack containing medication for one aerosol treatment.

30. An apparatus as recited in claim 29, wherein said cartridge is disposable.

31. An apparatus as recited in claim 29, further comprising:
  an actuator handle coupled to said actuator valve;
  wherein said actuator handle is configured to receive said cartridge.

32. An apparatus as recited in claim 31, wherein insertion of said cartridge into said actuator handle causes said nozzle to be sealed with an outlet passage of said reservoir containing compressed gas upon actuation of the actuator handle.

33. An apparatus as recited in claim 31, wherein insertion of said cartridge into said actuator handle causes said blister pack to be punctured.

34. An apparatus as recited in claim 31, wherein medication in said blister pack is entrained and aerosolized by said nozzle upon actuation of said actuator handle.

35. An inhaler apparatus, comprising:
  a reservoir for containing compressed gas;
  a jet orifice configured to receive compressed gas from said reservoir;
  a sonic shock chamber configured to receive compressed gas discharged from said jet orifice; and
  a user actuated valve configured to release said compressed gas in bursts for delivery to said supersonic shock nozzle;
  wherein said jet orifice is configured to produce a supersonic jet from said compressed gas;
  wherein said shock chamber is configured to receive said supersonic jet and produce shock waves;
  wherein upon formation of said supersonic jet and resulting shock waves in said shock chamber, a vacuum is generated which causes liquid from a liquid reservoir to be entrained through a liquid feed into said shock chamber;
  wherein upon entrainment of liquid into the shock chamber, the initial liquid entrained comes in contact with shock waves, producing copious amounts of aerosol particles suitable for inhalation; and
  wherein once liquid has been entrained into the shock chamber and supersonic jet, the integrity of the supersonic jet and resulting reflecting shock waves is destroyed, resulting in less subsequent production of aerosol particles than the initial burst and generally a larger particle size.

36. An apparatus as recited in claim 35, wherein if said supersonic jet is over expanded or under expanded, said supersonic jet will establish a series of reflected compression and expansion shock waves in said shock chamber.

37. An apparatus as recited in claim 36, wherein said supersonic jet will be approximately the diameter of the jet orifice and travel down the axis of the shock chamber.

38. An apparatus as recited in claim 35, wherein if said supersonic jet is perfectly expanded, a cylindrical shock wave will be generated in said shock chamber that envelopes the entire jet.

39. An apparatus as recited in claim 35, further comprising:
  a cartridge containing said supersonic shock nozzle and a blister pack containing medication for one aerosol treatment.

40. An apparatus as recited in claim 39, wherein said cartridge is disposable.

41. An apparatus as recited in claim 39, further comprising:
  an actuator handle coupled to said actuator valve;
  wherein said actuator handle is configured to receive said cartridge.

42. An apparatus as recited in claim 41, wherein insertion of said cartridge into said actuator handle causes said nozzle to be sealed with an outlet passage of said reservoir containing compressed gas upon actuation of the actuator handle.

43. An apparatus as recited in claim 41, wherein insertion of said cartridge into said actuator handle causes said blister pack to be punctured.

44. An apparatus as recited in claim 41, wherein medication in said blister pack is entrained and aerosolized by said nozzle upon actuation of said actuator handle.

45. An inhaler apparatus, comprising:
  a reservoir for containing compressed gas;
  a jet orifice configured to receive compressed gas from said reservoir and produce a supersonic jet;
  a sonic shock chamber configured to receive said supersonic jet and produce shock waves; and
  a user actuated valve configured to release said compressed gas in bursts for delivery to said supersonic shock nozzle;
  wherein if said supersonic jet is over expanded or under expanded, said supersonic jet will establish a series of reflected compression and expansion shock waves in said shock chamber.

46. An apparatus as recited in claim 45, wherein said supersonic jet will be approximately the diameter of the jet orifice and travel down the axis of the shock chamber.

47. An apparatus as recited in claim 45, wherein if said supersonic jet is perfectly expanded, a cylindrical shock wave will be generated in said shock chamber that envelopes the entire jet.

48. An apparatus as recited in claim 45, wherein upon formation of said supersonic jet and resulting shock waves in said shock chamber, a vacuum is generated which causes liquid from a liquid reservoir to be entrained through a liquid feed into said shock chamber.

49. An apparatus as recited in claim 48, wherein upon entrainment of liquid into the shock chamber, the initial liquid entrained comes in contact with shock waves, producing copious amounts of aerosol particles suitable for inhalation.

50. An apparatus as recited in claim 49, wherein once liquid has been entrained into the shock chamber and supersonic jet, the integrity of the supersonic jet and resulting reflecting shock waves is destroyed, resulting in less subsequent production of aerosol particles than the initial burst and generally a larger particle size.

51. An apparatus as recited in claim 45, further comprising:
a cartridge containing said jet orifice, said shock chamber, and a blister pack containing medication for one aerosol treatment.

52. An apparatus as recited in claim 51, wherein said cartridge is disposable.

53. An apparatus as recited in claim 51, further comprising:
an actuator handle coupled to said actuator valve;
wherein said actuator handle is configured to receive said cartridge.

54. An apparatus as recited in claim 53, wherein insertion of said cartridge into said actuator handle causes said nozzle to be sealed with an outlet passage of said reservoir containing compressed gas upon actuation of the actuator handle.

55. An apparatus as recited in claim 53, wherein insertion of said cartridge into said actuator handle causes said blister pack to be punctured.

56. An apparatus as recited in claim 53, wherein medication in said blister pack is entrained and aerosolized by said nozzle upon actuation of said actuator handle.

57. An inhaler apparatus, comprising:
a reservoir for containing compressed gas;
a jet orifice configured to receive compressed gas from said reservoir and produce a supersonic jet;
a sonic shock chamber configured to receive said supersonic jet and produce shock waves; and
a user actuated valve configured to release said compressed gas in bursts for delivery to said supersonic shock nozzle;
wherein upon formation of said supersonic jet and resulting shock waves in said shock chamber, a vacuum is generated which causes liquid from a liquid reservoir to be entrained through a liquid feed into said shock chamber;
wherein upon entrainment of liquid into the shock chamber, the initial liquid entrained comes in contact with shock waves, producing copious amounts of aerosol particles suitable for inhalation; and
wherein once liquid has been entrained into the shock chamber and supersonic jet, the integrity of the supersonic jet and resulting reflecting shock waves is destroyed, resulting in less subsequent production of aerosol particles than the initial burst and generally a larger particle size.

58. An apparatus as recited in claim 57, wherein if said supersonic jet is over expanded or under expanded, said supersonic jet will establish a series of reflected compression and expansion shock waves in said shock chamber.

59. An apparatus as recited in claim 58, wherein said supersonic jet will be approximately the diameter of the jet orifice and travel down the axis of the shock chamber.

60. An apparatus as recited in claim 57, wherein if said supersonic jet is perfectly expanded, a cylindrical shock wave will be generated in said shock chamber that envelopes the entire jet.

61. An apparatus as recited in claim 57, further comprising:
a cartridge containing said jet orifice, said shock chamber, and a blister pack containing medication for one aerosol treatment.

62. An apparatus as recited in claim 61, wherein said cartridge is disposable.

63. An apparatus as recited in claim 61, further comprising:
an actuator handle coupled to said actuator valve;
wherein said actuator handle is configured to receive said cartridge.

64. An apparatus as recited in claim 63, wherein insertion of said cartridge into said actuator handle causes said nozzle to be sealed with an outlet passage of said reservoir containing compressed gas upon actuation of the actuator handle.

65. An apparatus as recited in claim 63, wherein insertion of said cartridge into said actuator handle causes said blister pack to be punctured.

66. An apparatus as recited in claim 63, wherein medication in said blister pack is entrained and aerosolized by said nozzle upon actuation of said actuator handle.

67. An inhaler apparatus, comprising:
a reservoir for containing compressed gas;
a jet orifice configured to receive compressed gas from said reservoir and produce a supersonic jet;
a sonic shock chamber configured to receive said supersonic jet and produce shock waves;
a valve configured to release said compressed gas in bursts for delivery to said supersonic shock nozzle; and
an actuator handle coupled to said valve;
wherein if said supersonic jet is over expanded or under expanded, said supersonic jet will establish a series of reflected compression and expansion shock waves in said shock chamber.

68. An apparatus as recited in claim 67, wherein said supersonic jet will be approximately the diameter of the jet orifice and travel down the axis of the shock chamber.

69. An apparatus as recited in claim 67, wherein if said supersonic jet is perfectly expanded, a cylindrical shock wave will be generated in said shock chamber that envelopes the entire jet.

70. An apparatus as recited in claim 67, wherein upon formation of said supersonic jet and resulting shock waves in said shock chamber, a vacuum is generated which causes liquid from a liquid reservoir to be entrained through a liquid feed into said shock chamber.

71. An apparatus as recited in claim 70, wherein upon entrainment of liquid into the shock chamber, the initial liquid entrained comes in contact with shock waves, producing copious amounts of aerosol particles suitable for inhalation.

72. An apparatus as recited in claim 71, wherein once liquid has been entrained into the shock chamber and supersonic jet, the integrity of the supersonic jet and resulting reflecting shock waves is destroyed, resulting in less subsequent production of aerosol particles than the initial burst and generally a larger particle size.

73. An apparatus as recited in claim 67, further comprising:
a cartridge containing said jet orifice, said shock chamber, and a blister pack containing medication for one aerosol treatment.

74. An apparatus as recited in claim 73, wherein said cartridge is disposable.

75. An apparatus as recited in claim 73, wherein said actuator handle is configured to receive said cartridge.

76. An apparatus as recited in claim 75, wherein insertion of said cartridge into said actuator handle causes said nozzle to be sealed with an outlet passage of said reservoir containing compressed gas upon actuation of the actuator handle.

77. An apparatus as recited in claim 75, wherein insertion of said cartridge into said actuator handle causes said blister pack to be punctured.

78. An apparatus as recited in claim 75, wherein medication in said blister pack is entrained and aerosolized by said nozzle upon actuation of said actuator handle.

79. An inhaler apparatus, comprising:

a reservoir for containing compressed gas;

a jet orifice configured to receive compressed gas from said reservoir and produce a supersonic jet;

a sonic shock chamber configured to receive said supersonic jet and produce shock waves;

a valve configured to release said compressed gas in bursts for delivery to said supersonic shock nozzle; and an actuator handle coupled to said valve;

wherein upon formation of said supersonic jet and resulting shock waves in said shock chamber, a vacuum is generated which causes liquid from a liquid reservoir to be entrained through a liquid feed into said shock chamber;

wherein upon entrainment of liquid into the shock chamber, the initial liquid entrained comes in contact with shock waves, producing copious amounts of aerosol particles suitable for inhalation; and wherein once liquid has been entrained into the shock chamber and supersonic jet, the integrity of the supersonic jet and resulting reflecting shock waves is destroyed, resulting in less subsequent production of aerosol particles than the initial burst and generally a larger particle size.

80. An apparatus as recited in claim 79, wherein if said supersonic jet is over expanded or under expanded, said supersonic jet will establish a series of reflected compression and expansion shock waves in said shock chamber.

81. An apparatus as recited in claim 80, wherein said supersonic jet will be approximately the diameter of the jet orifice and travel down the axis of the shock chamber.

82. An apparatus as recited in claim 79, wherein if said supersonic jet is perfectly expanded, a cylindrical shock wave will be generated in said shock chamber that envelopes the entire jet.

83. An apparatus as recited in claim 79, further comprising:

a cartridge containing said jet orifice, said shock chamber, and a blister pack containing medication for one aerosol treatment.

84. An apparatus as recited in claim 83, wherein said cartridge is disposable.

85. An apparatus as recited in claim 83, wherein said actuator handle is configured to receive said cartridge.

86. An apparatus as recited in claim 85, wherein insertion of said cartridge into said actuator handle causes said nozzle to be sealed with an outlet passage of said reservoir containing compressed gas upon actuation of the actuator handle.

87. An apparatus as recited in claim 85, wherein insertion of said cartridge into said actuator handle causes said blister pack to be punctured.

88. An apparatus as recited in claim 85, wherein medication in said blister pack is entrained and aerosolized by said nozzle upon actuation of said actuator handle.

* * * * *